United States Patent [19]

Urdea et al.

[11] Patent Number: 5,124,246

[45] Date of Patent: Jun. 23, 1992

[54] NUCLEIC ACID MULTIMERS AND AMPLIFIED NUCLEIC ACID HYBRIDIZATION ASSAYS USING SAME

[75] Inventors: Michael S. Urdea, Alamo; Brian Warner, Martinez; Thomas Horn, Berkeley, all of Calif.

[73] Assignee: Chiron Corporation, Emeryville, Calif.

[21] Appl. No.: 340,031

[22] Filed: Apr. 18, 1989

Related U.S. Application Data

[63] Continuation-in-part of Ser. No. 252,638, Sep. 30, 1988, abandoned, which is a continuation-in-part of Ser. No. 185,201, Apr. 22, 1988, abandoned, which is a continuation-in-part of Ser. No. 109,282, Oct. 15, 1987, abandoned.

[51] Int. Cl.$^5$ .................... C12Q 1/68; C07H 21/00
[52] U.S. Cl. ........................ 435/6; 435/810; 436/501; 935/23; 935/78; 935/88; 536/27
[58] Field of Search ............ 435/6, 810; 436/501; 536/27; 935/23, 78, 88

[56] References Cited

U.S. PATENT DOCUMENTS

| | | | |
|---|---|---|---|
| 4,358,535 | 11/1982 | Falkow et al. | 435/5 |
| 4,670,379 | 6/1987 | Miller | 435/6 |
| 4,683,202 | 7/1987 | Mullis | 435/91 |
| 4,687,732 | 8/1987 | Ward et al. | 435/6 |
| 4,689,295 | 8/1987 | Taber et al. | 435/6 |
| 4,734,363 | 3/1988 | Dattagupta et al. | 435/91 |
| 4,797,355 | 1/1989 | Stabinsky | 435/6 |
| 4,800,159 | 1/1989 | Mullis et al. | 435/172.3 |
| 4,808,519 | 2/1989 | Hartley et al. | 435/6 |
| 4,808,520 | 2/1989 | Dattagupta et al. | 435/6 |
| 4,828,979 | 5/1989 | Klevan et al. | 435/6 |

FOREIGN PATENT DOCUMENTS

| | | |
|---|---|---|
| 229701 | 7/1922 | European Pat. Off. |
| 153873 | 9/1985 | European Pat. Off. |
| 159719 | 10/1985 | European Pat. Off. |
| 173339 | 3/1986 | European Pat. Off. |
| 185494 | 6/1986 | European Pat. Off. |
| 192168 | 8/1986 | European Pat. Off. |
| 0204510 | 12/1986 | European Pat. Off. |
| 237362 | 9/1987 | European Pat. Off. |
| 237737 | 9/1987 | European Pat. Off. |
| 238332 | 9/1987 | European Pat. Off. |
| 225807 | 6/1989 | European Pat. Off. |
| 3420925A1 | 12/1985 | Fed. Rep. of Germany |
| 84/03520 | 9/1984 | PCT Int'l Appl. |
| 124221 | 11/1984 | PCT Int'l Appl. |
| 85/00813 | 2/1985 | PCT Int'l Appl. |
| 86/07387 | 12/1986 | PCT Int'l Appl. |
| 87/03621 | 6/1987 | PCT Int'l Appl. |
| 87/03622 | 6/1987 | PCT Int'l Appl. |
| 87/03911 | 7/1987 | PCT Int'l Appl. |
| 87/05334 | 9/1987 | PCT Int'l Appl. |
| 2156074A | 10/1985 | United Kingdom |

OTHER PUBLICATIONS

Kiyama et al. (1986) *Proc. Natl Acad Sci (USA)* vol. 83, pp. 4665–4669.
Stanley et al., (1987) *Nature* 274:87–89.
Wilson et al., (1985) *Gene Anal Techn* 2:77–82.
Ouellette et al., (1987) *Can J Microbiol* 33:205–211.
Bell et al., (1983) *Analyt Biochem* 130:527–535.
Sekine et al., (1985) *Nucleic Acids Res* 16:185–188.
Ma et al., (1986) *Nucleic Acid Res* 14:9745–9753.
Tomalia et al., (1986) *Macromolecules* 19:2466–2468.
Padias et al., (1987) *J Org Chem* 52:5305–5312.
Tomalia et al., (1987) *Macromolecules* 20:1164–1167.
Tomalia et al., (1987) *J Am Chem Soc* 109:1601–1603.
Newkome et al., (1986) *J Chem Soc, Chem Commun* 118:752–753.
Welcher et al., (1986) *Nucleic Acids Research* 14:10027–10044.
Urdea et al., (1987) *Gene* 61:253–264.
Worthy, Ward (Feb. 22, 1988) *C&EN*:19–21.
Naylor et al., (1989) *J Am Chem Soc* 111:2339–2341.
Posnett et al., (1988) *J Biol Chem* 263:1719–1725.
Guo et al., (1989) *Biochemistry* 28:2355–2359.
Lim et al., (1989) *Cell* 56:891–904.
Foldesi et al., (1989) *Tetrahedron Letters* 30:881–884.
Zhou et al., (1988) *Tetrahedron* 44:6471–6489.
Balgobin et al., (1988) *Tetrahedron* 44:6929–6939.
Damha et al., (1988) *J Org Chem* 53:3710–3722.
Huss et al., (1988) *J Org Chem* 53:499–506.
Petrillo et al., in *Biopolymers* vol. 27:1337–1352 John Wiley & Sons, Inc. (1988).

*Primary Examiner*—Robert A. Wax

● = FORK-TYPE BRANCHING MONOMER (bis-DMT)
■ = COMB-TYPE BRANCHING MONOMER (5'-DMT, N$^4$-HYDROXYHEXYL-FMOC)

*Assistant Examiner*—Ardin H. Marschel
*Attorney, Agent, or Firm*—Morrison & Foerster

[57] ABSTRACT

Linear or branched oligonucleotide multimers useful as amplifiers in biochemical assays which comprise (1) at least one first single-stranded oligonucleotide unit that is complementary to a single-stranded oligonucleotide sequence of interest, and (2) a multiplicity of second single-stranded oligonucleotide units that are complementary to a single-stranded labeled oligonucleotide. Amplified sandwich nucleic acid hybridizations and immunoassays using the multimers are exemplified.

59 Claims, 22 Drawing Sheets

WHERE: OH ———⊞P = LOWER STRAND COMPLEMENT WITH PHOSPHORYLATED 5' END.

⊞———OH = UPPER STRAND COMPLEMENT NOT PHOSPHORYLATED AT THE 5' END.

WHERE:

= 4-AMINOETHYLAMINO CYTIDINE MODIFIED BASE INCORPORATED INTO SYNTHETIC OLIGONUCLEOTIDE

A. Linear synthetic DNA.
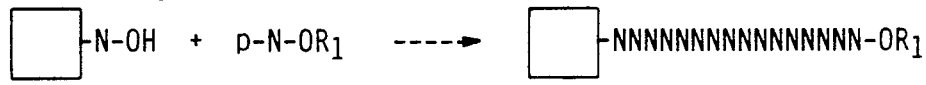
B. Branched DNA, comb structures.
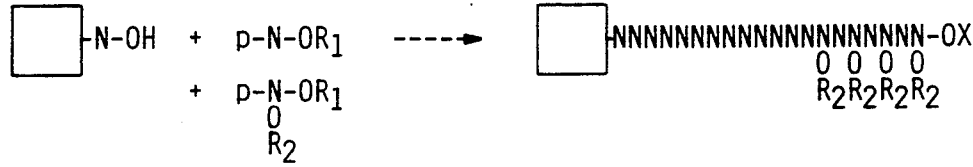
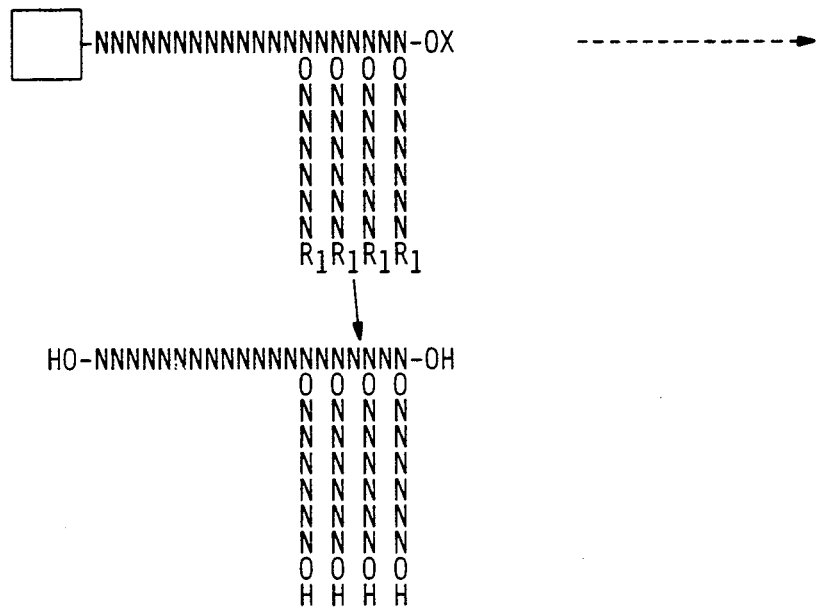
C. Branched DNA, fork structures.
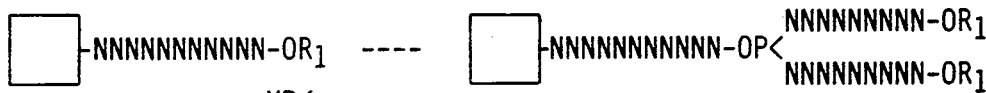
FIG. 3-1

D. Multiple Forks (through solution assembly).
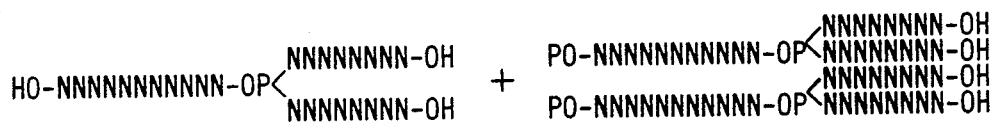
1) Splicing linker used for T4 ligase.
2) Chemical ligation also posssible.
E. Forked comb structures
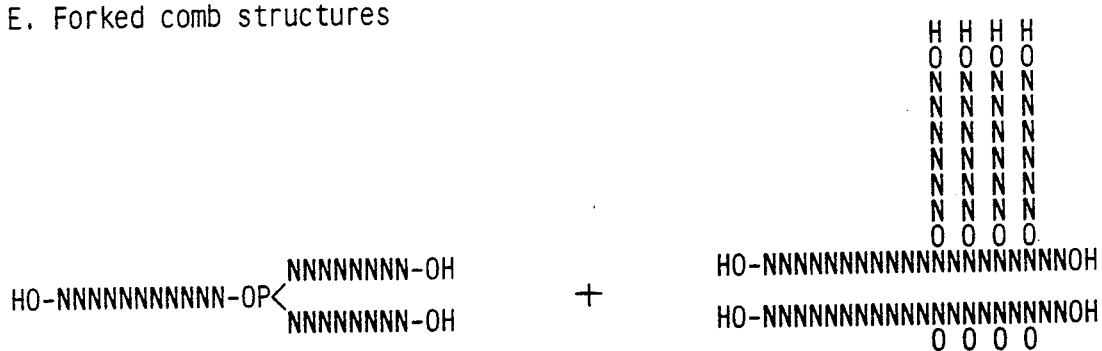
1) Splicing linker used for T4 ligase assembly.
2) Chemical assembly also possible.
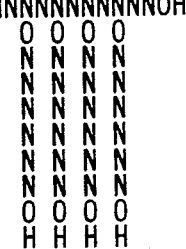
FIG. 3-2

F. Multiple Comb Structure

● = FORK-TYPE BRANCHING MONOMER (bis-DMT)
■ = COMB-TYPE BRANCHING MONOMER (5'-DMT, $N^4$-HYDROXYHEXYL-FMOC)

FIG. 10

Sequences of the complementary strand of the N.gonorrhoeae Tem-1 beta lactamase gene. Coding only. Thirty bases with the amplifier 20mer 11a2c TTAGGCATAGGACCCGTGTC added at the 3' end, discarded 3 and continued. All the sequences are 5' to 3'.

CCAATGCTTAATCAGTGAGGCACCTATCTC
TTAGGCATAGGACCCGTGTC

GATCTGTCTATTTCGTTCATCCATAGTTGC
TTAGGCATAGGACCCGTGTC

ACTCCCCGTCGTGTAGATAACTACGATACG
TTAGGCATAGGACCCGTGTC

GGGCTTACCATCTGGCCCCAGTGCTGCAAT
TTAGGCATAGGACCCGTGTC

ACCGCGAGACCCACGCTCACCGGCTCCAGA
TTAGGCATAGGACCCGTGTC

ATCAGCAATAAACCAGCCAGCCGGAAGGGC
TTAGGCATAGGACCCGTGTC

GCGCAGAAGTGGTCCTGCAACTTTATCCGC
TTAGGCATAGGACCCGTGTC

CATCCAGTCTATTAATTGTTGCCGGGAAGC
TTAGGCATAGGACCCGTGTC

AGTAAGTAGTTCGCCAGTTAATAGTTTGCG
TTAGGCATAGGACCCGTGTC

CGTTGTTGCCATTGCTGCAGGCATCGTGGT
TTAGGCATAGGACCCGTGTC

ACGCTCGTCGTTTGGTATGGCTTCATTCAG
TTAGGCATAGGACCCGTGTC

CGGTTCCCAACGATCAAGGCGAGTTACATG
TTAGGCATAGGACCCGTGTC

CCCCATGTTGTGCAAAAAAGCGGTTAGCTC
TTAGGCATAGGACCCGTGTC

CGGTCCTCCGATCGTTGTCAGAAGTAAGTT
TTAGGCATAGGACCCGTGTC

CGCAGTGTTATCACTCATGGTTATGGCAGC
TTAGGCATAGGACCCGTGTC

GCATAATTCTCTTACTGTCATGCCATCCGT
TTAGGCATAGGACCCGTGTC

ATGCTTTTCTGTGACTGGTGAGTACTCAAC
TTAGGCATAGGACCCGTGTC

GTCATTCTGAGAATAGTGTATGCGGCGACC
TTAGGCATAGGACCCGTGTC

TTGCTCTTGCCCGGCGTCAACACGGGATAA
TTAGGCATAGGACCCGTGTC

FIG.11-1

CGCGCCACATAGCAGAACTTTAAAAGTGCT
TTAGGCATAGGACCCGTGTC

CATTGGAAAACGTTCTTCGGGGCGAAAACT
TTAGGCATAGGACCCGTGTC

AAGGATCTTACCGCTGTTGAGATCCAGTTC
TTAGGCATAGGACCCGTGTC

GTAACCCACTCGTGCACCCAACTGATCTTC
TTAGGCATAGGACCCGTGTC

ATCTTTTACTTTCACCAGCGTTTCTGGGTG
TTAGGCATAGGACCCGTGTC

AAAAACAGGAAGGCAAAATGCCGCAAAAAA
TTAGGCATAGGACCCGTGTC

AATAAGGGCGACACGGAAATGTTGAATACT
TTAGGCATAGGACCCGTGTC

Complementary sequences of the N.gonorrhoeae 7.2 kb plasmid downstream of the coding region of beta lactamase. All sequences are 5' to 3' and EVERY SEQUENCE has the xt1 capture sequence.

AACGAGAAATCTGATTTAGTCGTTGAGGTT
CTTCTTTGGAGAAAGTGGTG

CAAATCAAGCGTGGGCGTACTATTCACTCT
CTTCTTTGGAGAAAGTGGTG

AATTTTGTGATTGGTAGTAAAAAACGAACA
CTTCTTTGGAGAAAGTGGTG

CAAAAAATTGAAGAAGTTGCAAACGGCCAG
CTTCTTTGGAGAAAGTGGTG

TTCCACATAAAAACAAGTATGGGAAGTTCG
CTTCTTTGGAGAAAGTGGTG

AACTCGATAAGCAAAACCCTAAGATGAGCA
CTTCTTTGGAGAAAGTGGTG

ACGAGTACGGTTTATGGGCTAGAGATTGCT
CTTCTTTGGAGAAAGTGGTG

AAATACTCGAAGATCATTACACAGATATTA
CTTCTTTGGAGAAAGTGGTG

AAGTTACCAATGAAGATTTGCGTAATTACT
CTTCTTTGGAGAAAGTGGTG

TATTTCTAGCGGGTAACGATAGCAATAGAT
CTTCTTTGGAGAAAGTGGTG

FIG.11-2

**** ALL SEQUENCES ARE SHOWN 3' TO 5'. ****

The first 20 bases of each sequence are the XT1 (capture) of LLA2C (amplifier) bases followed by 30 bases of the gene. Between each primer there are 3 bases left out for spacers. The sequences are to be called tn3kit.(1 thru 26).

XT1 (capture):     GTG GTG AAA GAG GTT TCT TC
LLA2C (amplifier):    CTG TGC CCA GGA TAC GGA TT 1.-   GTG GTG AAA GAG GTT TCT TCT ACT CAT AAG TTG TAA AGG CAC AGC GGG AA
2.-   CTG TGC CCA GGA TAC GGA TTG GGA AAA AAC GCC GTA AAA CGG AAG GAC AA
3.-   CTG TGC CCA GGA TAC GGA TTC GAG TGG GTC TTT GCG ACC ACT TTC ATT TT
4.-   CTG TGC CCA GGA TAC GGA TTC GAC TTC TAG TCA ACC CAC GTG CTC ACC CA
5.-   GTG GTG AAA GAG GTT TCT TCT AGC TTG ACC TAG AGT TGT CGC CAT TCT AG
6.-   CTG TGC CCA GGA TAC GGA TTC TCT CAA AAG CGG GGC TTC TTG CAA AAG GT
7.-   CTG TGC CCA GGA TAC GGA TTT ACT CGT GAA AAT TTC AAG ACG ATA CAC CG
8.-   CTG TGC CCA GGA TAC GGA TTC ATA ATA GGG CAC AAC TGC GGC CCG TTC TC
9.-   GTG GTG AAA GAG GTT TCT TCG AGC CAG CGG CGT ATG TGA TAA GAG TCT TA
10.-  CTG TGC CCA GGA TAC GGA TTA ACC AAC TCA TGA GTG GTC AGT GTC TTT TC
11.-  CTG TGC CCA GGA TAC GGA TTG AAT GCC TAC CGT ACT GTC ATT CTC TTA AT
12.-  CTG TGC CCA GGA TAC GGA TTT CAC GAC GGT ATT GGT ACT CAC TAT TGT GA
13.-  GTG GTG AAA GAG GTT TCT TCC GGT TGA ATG AAG ACT GTT GCT AGC CTC CT
14.-  CTG TGC CCA GGA TAC GGA TTT TCC TCG ATT GGC GAA AAA ACG TGT TGT AC
15.-  CTG TGC CCA GGA TAC GGA TTC TAG TAC ATT GAG CGG AAC TAG CAA CCC TT
16.-  CTG TGC CCA GGA TAC GGA TTC TCG ACT TAC TTC GGT ATG GTT TGC TGC TC
17.-  GTG GTG AAA GAG GTT TCT TCC TGT GGT GCT ACG GAC GTC GTT ACC GTT GT
18.-  CTG TGC CCA GGA TAC GGA TTA ACG CGT TTG ATA ATT GAC CGC TTG ATG AA
19.-  CTG TGC CCA GGA TAC GGA TTG ATC GAA GGG CCG TTG TTA ATT ATC TGA CC
20.-  CTG TGC CCA GGA TAC GGA TTC TCC GCC TAT TTC AAC GTC CTG GTG AAG AC
21.-  GTG GTG AAA GAG GTT TCT TCA GCC GGG AAG GCC GAC CGA CCA AAT AAC GA
22.-  CTG TGC CCA GGA TAC GGA TTT TTA GAC CTC GGC CAC TCG CAC CCA GAG CG
23.-  CTG TGC CCA GGA TAC GGA TTT AGT AAC GTC GTG ACC CCG GTC TAC CAT TC
24.-  CTG TGC CCA GGA TAC GGA TTA GGG CAT AGC ATC AAT AGA TGT GCT GCC CC
25.-  GTG GTG AAA GAG GTT TCT TCG TCC GTT GAT ACC TAC TTG CTT TAT CTG TC
26.-  CTG TGC CCA GGA TAC GGA TTC GAC TCT ATC CAC GGA GTG ACT AAT TCG TA

FIG. 12

```
xt1:    CTTCTTTGGAGAAAGTGGTG
LLA2c:  TTAGGCATAGGACCCGTGTC
```

```
  1  GATTCTAAAGTATCCGGACAATATCTGTATGCTTTGTATGCCTATGGTTATGCATAAAAAT

62  CCCAGTGATAAGAGTATTTATCACTGGGATTTTTATGCCCTTTTGGGCTTTTGAATGGAG

MetLysIleIleAsnIleGlyValLeuAlaHisValAspAlaGlyLysThr
122  GAAAATCACATGAAAATTATTAATATTGGAGTTTTAGCTCATGTTGATGCGGGAAAAACT
                 CTTTTAATAATTATAACCTCAAAATCGAGT  ACTACGCCCTTTTGA
                 B58                             A57

ThrLeuThrGluSerLeuLeuTyrAsnSerGlyAlaIleThrGluLeuGlySerValAsp
182  ACCTTAACAGAAAGCTTATTATATAACAGTGGAGCGATTACAGAATTAGGAAGCGTGGAC
     TGGAATTGTCTTTC   TAATATATTGTCACCTCGCTAATGTCTTAA   TTCGCACCTG
                  B56                                B55

ArgGlyThrThrLysThrAspAsnThrLeuLeuGluArgGlnArgGlyIleThrIleGln
242  AGAGGTACAACGAAAACGGATAATACGCTTTTAGAACGTCAGAGAGGAATTACAATTCAG
     TCTCCATGTTGCTTTTGCCT    ATGCGAAAATCTTGCAGTCTCTCCTTAATG    AGTC
                        B54                                  A53

ThrAlaIleThrSerPheGlnTrpLysAsnThrLysValAsnIleIleAspThrProGly
302  ACGGCGATAACCTCTTTTCAGTGGAAAAATACTAAGGTGAACATCATAGACACGCCAGGA
     TGCCGCTATTGGAGAAAAGTCACCTT    ATGATTCCACTTGTAGTATCTGTGCGGTCC
                              B52

HisMetAspPheLeuAlaGluValTyrArgSerLeuSerValLeuAspGlyAlaIleLeu
362  CATATGGATTTTTTAGCAGAAGTATATCGTTCATTATCAGTATTAGATGGGGCAATTCTA
        ATACCTAAAAAATCGTCTTCATATAGCAAG   TAGTCATAATCTACCCCGTTAAGAT
        B51                              B50

LeuIleSerAlaLysAspGlyValGlnAlaGlnThrArgIleLeuPheHisAlaLeuArg
422  CTGATTTCTGCAAAAGATGGCGTACAAGCACAAACTCGTATATTGTTTCATGCACTTAGG
     GACTA   ACGTTTTCTACCGCATGTTCGTGTTTGAGC   TAACAAAGTACGTGAATCC
          A49                                B48

LysIleGlyIleProThrIlePhePheIleAsnLysIleAspGlnAsnGlyIleAspLeu
482  AAAATAGGTATTCCCACAATCTTTTTTATCAATAAGATTGACCAAAATGGAATTGATTTA
     TTTTATCCATA    GTGTTAGAAAAAATAGTTATTCTAACTGGT    ACCTTAACTAAAT
                B47                                 B46

SerThrValTyrGlnAspIleLysGluLysLeuSerAlaGluIleValIleLysGlnLys
542  TCAACGGTTTATCAGGATATTAAAGAGAAACTTTCTGCGGAAATTGTAATCAAACAGAAG
     AGTTGCCAAATAGTCCT    ATTTCTCTTTGAAAGACGCCTTTAACATTA    TGTCTTC
                     A45                                  B44

ValGluLeuHisProAsnMetArgValMetAsnPheThrGluSerGluGlnTrpAspMet
602  GTAGAACTGCATCCTAATATGCGTGTAATGAACTTTACCGAATCTGAACAATGGGATATG
     CATCTTGACGTAGGATTATACGC    TTACTTGAAATGGCTTAGACTTGTTACCCT    C
                            B43                                  B
```

FIG.13-1

```
       ValIleGluGlyAsnAspTyrLeuLeuGluLysTyrThrSerGlyLysLeuLeuGluAla
 662   GTAATAGAAGGAAATGATTACCTTTTGGAGAAATATACGTCTGGGAAATTATTGGAAGCA
       CATTATCTTCCTTTACTAATGGAAAACCT   TATATGCAGACCCTTTAATAACCTTCGT
       42                              A41

LeuGluLeuGluGlnGluGluSerIleArgPheHisAsnCysSerLeuPheProValTyr
 722   TTAGAACTCGAACAAGAGGAAAGCATAAGATTTCATAATTGTTCCCTGTTCCCTGTTTAT
       AA   TGAGCTTGTTCTCCTTTCGTATTCTAAAGT   AACAAGGGACAAGGGACAAATA
            B40                              B39

HisGlySerAlaLysAsnAsnIleGlyIleAspAsnLeuIleGluValIleThrAsnLys
 782   CACGGAAGTGCAAAAAACAATATAGGGATTGATAACCTTATAGAAGTGATTACGAATAAA
       GTGCCTTC   TTTTTTGTTATATCCCTAACTATTGGAATA   TCACTAATGCTTATTT
                  B38                              A37

PheTyrSerSerThrHisArgGlyGlnSerGluLeuCysGlyLysValPheLysIleGlu
 842   TTTTATTCATCAACACATCGAGGTCAGTCTGAACTTTGCGGAAAAGTTTTCAAAATTGAG
       AAAATAAGTAGTTG   AGCTCCAGTCAGACTTGAAACGCCTTTTCA   GTTTTAACTC
                      B36                              B35

TyrSerGluLysArgGlnArgLeuAlaTyrIleArgLeuTyrSerGlyValLeuHisLeu
 902   TATTCGGAAAAAAGACAGCGTCTTGCATATATACGTCTTTATAGTGGCGTACTGCATTTG
       ATAAGCCTTTTTTCTGTCGC   ACGTATATATGCAGAAATATCACCGCATGA   AAAC
                            B34                              A33

ArgAspProValArgIleSerGluLysGluLysIleLysIleThrGluMetTyrThrSer
 962   CGAGATCCGGTTAGAATATCGGAAAAGGAAAAAATAAAAATTACAGAAATGTATACTTCA
       GCTCTAGGCCAATCTTATAGCCTTTT   TTTTTATTTTTAATGTCTTTACATATGAAG
                                    B32

IleAsnGlyGluLeuCysLysIleAspLysAlaTyrSerGlyGluIleValIleLeuGln
1022   ATAAATGGTGAATTATGTAAAATCGATAAGGCTTATTCCGGGGAAATTGTTATTTTGCAG
          TTTACCACTTAATACATTTTAGCTATTCCG   AAGGCCCCTTTAACAATAAAACGTC
           B31                              B30

AsnGluPheLeuLysLeuAsnSerValLeuGlyAspThrLysLeuLeuProGlnArgGlu
1082   AATGAGTTTTTGAAGTTAAATAGTGTTCTTGGAGATACAAAGCTATTGCCACAGAGAGAG
       TTACT   AAACTTCAATTTATCACAAGAACCTCTATG   CGATAACGGTGTCTCTCTC
               A29                              B28

ArgIleGluAsnProLeuProLeuLeuGlnThrThrValGluProSerLysProGlnGln
1142   AGAATTGAAAATCCCCTCCCTCTGCTGCAAACGACTGTTGAACCGAGCAAACCTCAACAA
       TCTTAACTTTT   GGAGGGAGACGACGTTTGCTGACAACTTGG   GTTTGGAGTTGTT
                    B27                              B26

ArgGluMetLeuLeuAspAlaLeuLeuGluIleSerAspSerAspProLeuLeuArgTyr
1202   AGGGAAATGTTACTTGATGCACTTTTAGAAATCTCCGACAGTGACCCGCTTCTGCGATAT
       TCCCTTTACAATGAACT   TGAAAATCTTTAGAGGCTGTCACTGGGCGA   CGCTATA
                          A25                              B24

TyrValAspSerAlaThrHisGluIleIleLeuSerPheLeuGlyLysValGlnMetGlu
1262   TATGTGGATTCTGCGACACATGAAATCATACTTTCTTTCTTAGGGAAAGTACAAATGGAA
       ATACACCTAAGACGCTGTGTACT   GTATGAAAGAAAGAATCCCTTTCATGTTTA   T
                                B23                              B

ValThrCysAlaLeuLeuGlnGluLysTyrHisValGluIleGluIleLysGluProThr
1322   GTGACTTGTGCTCTGCTGCAAGAAAAGTATCATGTGGAGATAGAAATAAAAGAGCCTACA
       CACTGAACACGAGACGACGTTCTTTTCAT   ACACCTCTATCTTTATTTTCTCGGATGT
       22                              A21

ValIleTyrMetGluArgProLeuLysLysAlaGluTyrThrIleHisIleGluValPro
1382   GTCATTTATATGGAAAGACCGTTAAAAAAAGCAGAGTATACCATTCACATCGAAGTTCCA
       CA   AATATACCTTTCTGGCAATTTTTTTCGTCT   ATGGTAAGTGTAGCTTCAAGGT
            B20                              B19
```

FIG.13-2

```
        ProAsnProPheTrpAlaSerIleGlyLeuSerValAlaProLeuProLeuGlySerGly
1442    CCGAATCCTTTCTGGGCTTCCATTGGTCTATCTGTAGCACCGCTTCCATTAGGGAGCGGA
        GGCTTAGG    GACCCGAAGGTAACCAGATAGACATCGTGG    AGGTAATCCCTCGCCT
              B18                                          A17

ValGlnTyrGluSerSerValSerLeuGlyTyrLeuAsnGlnSerPheGlnAsnAlaVal
1502    GTACAGTATGAGAGCTCGGTTTCTCTTGGATACTTAAATCAATCGTTTCAAAATGCAGTT
        CATGTCATACTCTC   CCAAAGAGAACCTATGAATTTAGTTAGCAA   TTTACGTCAA
              B16                                             B15

MetGluGlyIleArgTyrGlyCysGluGlnGlyLeuTyrGlyTrpAsnValThrAspCys
1562    ATGGAGGGGATACGCTATGGCTGTGAACAAGGATTGTATGGTTGGAATGTGACGGACTGT
        TACCTCCCCTATGCGATACC   ACTTGTTCCTAACATACCAACCTTACACTG   GACA
              B14                                                 A13

LysIleCysPheLysTyrGlyLeuTyrTyrSerProValSerThrProAlaAspPheArg
1622    AAAATCTGTTTTAAGTATGGCTTATACTATAGCCCTGTTAGTACCCCAGCAGATTTTCGG
        TTTTAGACAAAATTCATACCGAATAT   ATCGGGACAATCATGGGGTCGTCTAAAAGC
                                            B12

MetLeuAlaProIleValLeuGluGlnValLeuLysLysAlaGlyThrGluLeuLeuGlu
1682    ATGCTTGCTCCTATTGTATTGGAACAAGTCTTAAAAAAAGCTGGAACAGAATTGTTAGAG
             CGAACGAGGATAACATAACCTTGTTCAGAA   TTTTCGACCTTGTCTTAACAATCTC
              B11                                    B10

ProTyrLeuSerPheLysIleTyrAlaProGlnGluTyrLeuSerArgAlaTyrAsnAsp
1742    CCATATCTGAGTTTTAAAATTTATGCGCCACAGGAATATCTTTCACGAGCATACAACGAT
        GGTAT   CTCAAAATTTTAAATACGCGGTGTCCTTAT   AAGTGCTCGTATGTTGCTA
              A9                                     B8

AlaProLysTyrCysAlaAsnIleValAspThrGlnLeuLysAsnAsnGluValIleLeu
1802    GCTCCTAAATATTGTGCGAACATCGTAGACACTCAATTGAAAAATAATGAGGTCATTCTT
        CGAGGATTTAT   ACGCTTGTAGCATCTGTGAGTTAACTTTTT   ACTCCAGTAAGAA
              B7                                            B6

SerGlyGluIleProAlaArgCysIleGlnGluTyrArgSerAspLeuThrPhePheThr
1862    AGTGGAGAAATCCCTGCTCGGTGTATTCAAGAATATCGTAGTGATTTAACTTTCTTTACA
        TCACCTCTTTAGGGACG   CACATAAGTTCTTATAGCATCACTAAATTG   GAAATGT
              A5                                                 B4

AsnGlyArgSerValCysLeuThrGluLeuLysGlyTyrHisValThrThrGlyGluPro
1922    AATGGACGTAGTGTTTGTTTAACAGAGTTAAAAGGGTACCATGTTACTACCGGTGAACCT
        TTACCTGCATCACAAACAAATTG   CAATTTTCCCATGGTACAATGATGGCCACT   A
                                         B3                        B

ValCysGlnProArgArgProAsnSerArgIleAspLysValArgTyrMetPheAsnLys
1982    GTTTGCCAGCCCCGTCGTCCAAATAGTCGGATAGATAAAGTACGATATATGTTCAATAAA
        CAAACGGTCGGGGCAGCAGGTTTATCAGC   TCTATTTCATGCTATATACAAGTTATTT
         2                                  A1

IleThrAM
2042    ATAACTTAGTGTATTTTATGTTGTTATATAAATATGGTTTCTTGTTAAATAAG
        TA
```

FIG. 13-3

1   AAGCTTGGGATGTCAGAATCTGCATATCTGCATGGAGGCAACCGGCAATTATTATGAAGA
    TTCGAACCCTACAGTCTTAGACGTATAGACGTACCTCCGTTGGCCGTTAATAATACTTCT

1 HIND111, 2 ALU1, 8 FOK1, 14 ALWN1, 16 HINF1, 31 NLA111, 35
     MNL1, 42 HPA11, 56 MBO11,

61  AGTTGCCGACTACTTCGCGCAGTATTACAGCGTTTACGTAGTGAACCCGCTGAAAATAAG
    TCAACGGCTGATGAAGCGCGTCATAATGTCGCAAATGCATCACTTGGGCGACTTTTATTC

76 THA1, 77 HHA1, 95 SNAB1, 96 MAE2, 107 NSPB11,

121 CAAGTATGCAGAAAGCAGGTTCAAGCGAACCAAAACAGGCAAACAGGATGCAAAACTGAT
    GTTCATACGTCTTTCGTCCAAGTTCGCTTGGTTTTGTCCGTTTGTCCTACGTTTTGACTA

160 TTHIII2, 166 FOK1, 167 SFAN1,

181 AGCGCAGTATTGCCGGTCGGCGAAAGAAAGCGAGCTTGTAAAGAGGCAGAAGCTACGGAC
    TCGCGTCATAACGGCCAGCCGCTTTCTTTCGCTCGAACATTTCTCCGTCTTCGATGCCTG

182 HHA1, 193 HPA11, 213 ALU1, 223 MNL1, 231 ALU1,

241 GAGCAATACAGGCTTTCACGGATGATCCTTTGCTGCGTTTTGTCGGCCTGCGGTCGATTA
    CTCGTTATGTCCGAAAGTGCCTACTAGGAAACGACGCAAAACAGCCGGACGCCAGCTAAT

260 FOK1, 264 BIN1 MBO1 SAU3A, 272 BBV FNU4H1, 285 HAE111, 2
    94 TAQ1,

301 CCAAGTACAAACGTTTTTATCCGCCCCACTCCACACCGTTTAGAAACAATACTTCAACCC
    GGTTCATGTTTGCAAAAATAGGCGGGGTGAGGTGTGGCAAATCTTTGTTATGAAGTTGGG

305 RSA1, 311 MAE2,

361 AAGGAAACCGTTACAAATGATCTCGGGCTGATTCCCATCCGTCTCATAATGCAGCTTTTC
    TTCCTTTGGCAATGTTTACTAGAGCCCGACTAAGGGTAGGCAGAGTATTACGTCGAAAAG

370 MAE3, 379 MBO1 SAU3A, 382 AVA1, 390 HINF1, 396 FOK1, 411
     BBV FNU4H1, 413 ALU1,

421 GTCCCCTTTGAAAAAATCGGCGACGACCGCTTCCGCCTCTTCAAGAGATTGGCTGATAAA
    CAGGGGAAACTTTTTTAGCCGCTGCTGGCGAAGGCGGAGAAGTTCTCTAACCGACTATTT

456 MNL1, 458 MBO11,

481 TAAAGCCGAACTACCAAAGCCGATCC
    ATTTCGGCTTGATGGTTTCGGCTAGG

FIG.14

:jk1.1(50)
ATCGGCTTTGGTAGTTCGGCTTTATTTATC    capture
CTTCTTTGGAGAAAGTGGTG

:jk1.2(50)
CAATCTCTTGAAGAGGCGGAAGCGGTCGTC    amplifier
TTAGGCATAGGACCCGTGTC

:jk1.3(50)
GATTTTTTCAAAGGGGACGAAAAGCTGCAT    amplifier
TTAGGCATAGGACCCGTGTC

:jk1.4(50)
GAGACGGATGGGAATCAGCCCGAGATCATT    amplifier
TTAGGCATAGGACCCGTGTC

:jk1.5(50)
AACGGTTTCCTTGGGTTGAAGTATTGTTTC    capture
CTTCTTTGGAGAAAGTGGTG

:jk1.6(50)
ACGGTGTGGAGTGGGGCGGATAAAAACGTT    amplifier
TTAGGCATAGGACCCGTGTC

:jk1.7(50)
ACTTGGTAATCGACCGCAGGCCGACAAAAC    amplifier
TTAGGCATAGGACCCGTGTC

:jk1.8(50)
GCAAAGGATCATCCGTGAAAGCCTGTATTG    amplifier
TTAGGCATAGGACCCGTGTC

:jk1.9(50)
GTCCGTAGCTTCTGCCTCTTTACAAGCTCG    capture
CTTCTTTGGAGAAAGTGGTG

:jk1.10(50)
TCTTTCGCCGACCGGCAATACTGCGCTATC    amplifier
TTAGGCATAGGACCCGTGTC

:jk1.11(50)
TTTGCATCCTGTTTGCCTGTTTTGGTTCGC    amplifier
TTAGGCATAGGACCCGTGTC

:jk1.12(50)
AACCTGCTTTCTGCATACTTGCTTATTTTC    amplifier
TTAGGCATAGGACCCGTGTC

:jk1.13(50)
GGGTTCACTACGTAAACGCTGTAATACTGC    capture
CTTCTTTGGAGAAAGTGGTG

:jk1.14(50)
AAGTAGTCGGCAACTTCTTCATAATAATTG    amplifier
TTAGGCATAGGACCCGTGTC

:jk1.15(50)
GTTGCCTCCATGCAGATATGCAGATTCTGA    amplifier
TTAGGCATAGGACCCGTGTC

FIG.15

:HBV.LLA2C.70
TGACTG[CG]CGATTGGT[GA]GAGGCAGG[AC]GGAGGTTAGGCATAGGACCCGTGTC

:HBV.LLA2C.69
CTTG[AT][CT]GGG[GA]TTGAAGTCCCAATCTGGATTTTAGGCATAGGACCCGTGTC

:HBV.LLA2C.68
GTTGCGTCAGCAAACACTTGGCA[CG]AGACC[AT]TTAGGCATAGGACCCGTGTC

:HBV.LLA2C.67
TAAGTTGGCGAGAAAGT[GA]AAAGCCTG[TC]TT[AC]TTAGGCATAGGACCCGTGTC

:HBV.LLA2C.66
GCAGCAAA[GA]CCCAAAAGACCCACAA[TG][TA]C[TG][TC]TTAGGCATAGGACCCGTGTC

:HBV.LLA2C.65
ATGTATACCCA[GA]AGACA[AG]AAGAAAATTGGTTTAGGCATAGGACCCGTGTC

:HBV.XT1.64
CTTGGCCCCCAATACCACATCATCCATATACTTCTTTGGAGAAAGTGGTG

:HBV.XT1.63
GAAAGCCAAACAGTGGGGGAAAGCCCTACGCTTCTTTGGAGAAAGTGGTG

:HBV.XT1.62
CACTGAACAAATGGCACTAGTAAACTGAGCCTTCTTTGGAGAAAGTGGTG

:HBV.XT1.61
GAGAAACGG[AG]CTGAGGCCC[AC]CTCCCATAGGCTTCTTTGGAGAAAGTGGTG

:HBV.XT1.60
[GC]CGAAAGCCCAGGA[CT]GATGGGATGGGAATACTTCTTTGGAGAAAGTGGTG

:HBV.LLA2C.59
TAGAGGACAAACGGGCAACATACCTTG[AG]TATTAGGCATAGGACCCGTGTC

:HBV.LLA2C.58
GATGAGGCATAGCAGCAGGATGAAGAGGAATTAGGCATAGGACCCGTGTC

:HBV.LLA2C.57
GATAAAACGCCGCAGACACATCCAGCGATATTAGGCATAGGACCCGTGTC

:HBV.LLA2C.56
GGACAA[AG]TTGGAGGACA[GA]GAGGTTGGTGAGTTAGGCATAGGACCCGTGTC

:HBV.LLA2C.55
TTGGAGGTTGGGGACTGCGAATTTTGGCCATTAGGCATAGGACCCGTGTC

:HBV.LLA2C.54
CCACCACGAGTCTAGACTCTG[CT]GGTATTGTTTAGGCATAGGACCCGTGTC

:HBV.LLA2C.53
GATTCTTGTCAACAAGAAAAACCCCGCCTGTTAGGCATAGGACCCGTGTC

:HBV.LLA2C.52
CACGAG[CA]AGGGGTCCTAGGAATCCTGATGTTTAGGCATAGGACCCGTGTC

:HBV.LLA2C.51
CAGGGTTTACTGTTCC[TG]GAACTGGAGCCACTTAGGCATAGGACCCGTGTC

:HBV.LLA2C.71
CAGGGTCCCCAGTCCTCG[AC]G[AG]AGATTGACGTTAGGCAGAGGACCCGTGTC

FIG.16-1

:HBV.LLA2C.72
CCGTTGCCGAGCAACGGGGTAAAGGTT[CA]A[GT]TTAGGCATAGGACCCGTGTC

:HBV.LLA2C.73
GGTTGCGTCAGCAAACACTTGGCA[GC]AGACCTTAGGCATAGGACCCGTGTC

:HBV.LLA2C.74
AGTTCCGCAGTATGGATCGGCAGA[CG]GAGCCTTAGGCATAGGACCCGTGTC

:HBV.LLA2C.75
CCAGACC[TG][CG]CTGCGAGCAAAACAAGC[TG]GCTTTAGGCATAGGACCCGTGTC

:HBV.LLA2C.76
CAGTTGGCAG[CT]ACA[CG]CCTAGCAGCCATGGATTAGGCATAGGACCCGTGTC

:HBV.LLA2C.77
GGGACGTA[AG]ACAAAGGACGTCCCGCG[AC]AGGTTAGGCATAGGACCCGTGTC

:HBV.LLA2C.78
CGAGA[ACG]GGGTCGTCCGC[AG]GGATTCAGCGCCTTAGGCATAGGACCCGTGTC

:HBV.LLA2C.79
CCGCGTAAAGAGAGGTGCGCCCCGTGGTCGTTAGGCATAGGACCCGTGTC

:HBV.LLA2C.80
ACACGG[TA]CCGGCAGATGAGAAGGCACAGACTTAGGCATAGGACCCGTGTC

:HBV.LLA2C.81
C[TG]CCATGC[AGT]ACGTGCAGAGGTGAAGCGAAGTTAGGCATAGGACCCGTGTC

:HBV.LLA2C.82
CAAGAGTCCTCTT[AG]TGTAAGACCTTGGGCATTAGGCATAGGACCCGTGTC

:HBV.LLA2C.83
AACA[AC]ACAGTCTTTGAAGTA[TG]GCCTCAAGGTTAGGCATAGGACCCGTGTC

:HBV.LLA2C.84
CTAATCTCCTCCCCCA[AG]CTCCTCCCAGTC[CT]TTAGGCATAGGACCCGTGTC

:HBV.LLA2C.85
TGCCTACAGCCTCCTA[AG]TACAAAGA[CT]C[AT]TTTTAGGCATAGGACCCGTGTC

:HBV.LLA2C.D44
GACATG[AT]ACA[AT]GAGATGATTAGGCAGAGG[GT]TTAGGCATAGGACCCGTGTC

:HBV.LLA2C.D46
CTTTATA[CA]GG[AG]TC[GA]ATGTCCATGCCCCAAATTAGGCATAGGACCCGTGTC

:HBV.LLA2C.D47
AAAA[AC]GAGAGTAACTCCACAG[AT][AT]GCTCCAATTAGGCATAGGACCCGTGTC

:HBV.LLA2C.86
AGGAGTGCGAATCCACACTCC[AG]AAAGA[GCT]ACTTAGGCATAGGACCCGTGTC

:HBV.LLA2C.87
TAA[GA]GATAGGGGCATTTGGTGGTCT[AG]TA[GA]GCTTAGGCATAGGACCCGTGTC

:HBV.LLA2C.88
TCGTCTAACAACAGTAGT[CT]TCCGGAAGTGTTTAGGCATAGGACCCGTGTC

:HBV.XT1.89
CGAGGCGAGGGAGTTCTTCTTCTAGGGGACCTTCTTTGGAGAAAGTGGTG

FIG.16-2

:HBV.XT1.90
TCTTCTGCGACGCGGCGAT[GT]GAGA[TC]CT[GT]CGTCTTCTTTGGAGAAAGTGGTG

:HBV.XT1.D13
GG[AG]ATACTAACATTGAGATTCCCGAGATTGCTTCTTTGGAGAAAGTGGTG

:HBV.XT1.D14
AGCCC[CA]GTAAAGTT[TC]CC[CG]ACCTTATGAGTCCTTCTTTGGAGAAAGTGGTG

:HBV.LLA2C.91
GCTGTAG[CA]TCTTGTTCCCAAGAATATGGTGTTAGGCATAGGACCCGTGTC

:HBV.LLA2C.92
[TC]GCCCTGAGCCTG[AC]GGGCTCCACCCCAAAATTAGGCATAGGACCCGTGTC

:HBV.XT1.45
CCCAAGGCACAGCTTGGAGGCTTGAACAGCTTCTTTGGAGAAAGTGGTG

[ ] indicates two-fold degenerative positions

FIG.16-3

NUCLEIC ACID MULTIMERS AND AMPLIFIED NUCLEIC ACID HYBRIDIZATION ASSAYS USING SAME

CROSS-REFERENCE TO RELATED APPLICATIONS

This application is a continuation-in-part of copending U.S. patent application Ser. No. 252,638, filed Sep. 30, 1988 and now abandoned, which in turn is a continuation-in-part of copending U.S. patent application Ser. No. 185,201, filed Apr. 22, 1988 and now abandoned, which in turn is a continuation-in-part of copending U.S. patent application Ser. No. 109,282, filed Oct. 15, 1987 and now abandoned. The disclosure of these related applications are incorporated herein by reference.

DESCRIPTION

1. Technical Field

This invention is in the fields of nucleic acid chemistry and biochemical assays. More particularly, it relates to novel nucleic acid multimers and nucleic acid hybridization assays.

2. Background Art

Nucleic acid hybridizations are now commonly used in genetic research, biomedical research and clinical diagnostics. In the basic nucleic acid hybridization assay, single-stranded analyte nucleic acid (either DNA or RNA) is hybridized to a labeled nucleic acid probe, and resulting labeled duplexes are detected. Both radioactive and nonradioactive labels have been used.

Variations of this basic scheme have been developed to facilitate separation of the duplexes to be detected from extraneous materials and/or to amplify the signal that is detected.

Copending commonly owned U.S. Ser. No. 807,624, filed Dec. 11, 1985, describes a solution-phase nucleic acid hybridization assay in which the analyte nucleic acid is hybridized to a labeling probe set and to a capturing probe set. The probe-analyte complex is coupled by hybridization with a solid-supported capture probe that is complementary to the capture probe set. This permits the analyte nucleic acid to be removed from solution as a solid phase complex. Having the analyte in the form of a solid phase complex facilitates subsequent separation steps in the assay. The labeling probe set is complementary to a labeled probe that is bound through hybridization to the solid phase/analyte complex.

PCT Application 84/03520 and EPA 124221 describe a DNA hybridization assay in which: (1) analyte is annealed to a single-stranded DNA probe that has a tail that is complementary to an enzyme-labeled oligonucleotide, and (2) the resulting tailed duplex is hybridized to an enzyme-labeled oligonucleotide. The Enzo Biochem "Bio-Bridge" labeling system appears to be similar to the system described in these two patent applications. The "Bio-Bridge" system uses terminal deoxynucleotide transferase to add unmodified 3,-polyT-tails to a DNA probe. The polyT-tailed probe is hybridized to the target DNA sequence and then to a biotin-modified polyA.

EPA 204510 describes a DNA hybridization assay in which analyte DNA is contacted with a probe that has a tail, such as a polyT-tail, an amplifier strand that has a sequence, e.g., a polyA sequence, that hybridizes to the tail of the probe and is capable of binding a plurality of labeled strands.

The main problem with these prior hybridization assays is that they lack sufficient specificity and/or signal to be useful for detecting very low levels of analyte. A primary object of the present invention is to provide an amplifier for use in nucleic acid hybridizations that provides a high reproducible gain in signal, a high reproducible signal-to-noise ratio and low nonspecific binding, that is itself reproducible, and that is capable of combining specifically with a "universal" signal moiety and an analyte at low concentrations to form a stable complex.

Other aspects are to provide improved hybridization assays for hepatitis B virus (HBV), *N. gonorrhoeae*, penicillin and tetracycline resistance in *N. gonorrhoeae*, and *Chlamydia trachomatis*.

DISCLOSURE OF THE INVENTION

One aspect of the invention is a nucleic acid multimer comprising:

(a) at least one first single-stranded oligonucleotide unit that is capable of binding specifically to a first single-stranded nucleotide sequence of interest; and (b) a multiplicity of second single-stranded oligonucleotide units that are capable of binding specifically to a second single-stranded nucleotide sequence of interest.

Another aspect of the invention is a nucleic acid hybridization assay in which (1) the above-described multimer is hybridized via the first oligonucleotide unit to single-stranded analyte nucleic acid or an oligonucleotide bound to the analyte or to another multimer bound to the analyte, and (2) a multiplicity of single-stranded labeled oligonucleotides are then hybridized to the multimer via the multiplicity of second oligonucleotide units.

Still another aspect of the invention is a synthetic oligonucleotide useful as an amplifier probe in a solution-phase sandwich hybridization assay for hepatitis B virus (HBV) comprising (a) a first segment having a nucleotide sequence complementary to a segment of the HBV genome and (b) a second segment having a nucleotide sequence complementary to an oligonucleotide unit of a nucleic acid multimer.

Yet another aspect of the invention is a synthetic oligonucleotide useful as a capture probe in a solution-phase sandwich hybridization assay for HBV comprising (a) a first segment having a nucleotide sequence complementary to a segment of the HBV genome and (b) a second segment having a nucleotide sequence complementary to an oligonucleotide bound to a solid phase.

Still another aspect of the invention is a synthetic oligonucleotide useful as an amplifier probe in a solution-phase sandwich hybridization assay for *N. gonorrhoeae* comprising (a) a first segment having a nucleotide sequence complementary to a segment of *N. gonorrhoeae* pilin DNA and (b) a second segment having a nucleotide sequence complementary to an oligonucleotide unit of a nucleic acid multimer.

Yet another aspect of the invention is a synthetic oligonucleotide useful as a capture probe in a solution-phase sandwich hybridization assay for *N. gonorrhoeae* comprising (a) a first segment having a nucleotide sequence complementary to a segment of *N. gonorrhoeae* pilin DNA and (b) a second segment having a nucleotide sequence complementary to an oligonucleotide bound to a solid phase.

Still another aspect of the invention is a synthetic oligonucleotide useful as an amplifier probe in a solution-phase sandwich hybridization assay for *N. gonorrhoeae* comprising (a) a first segment having a nucleotide sequence complementary to a segment of the *N. gonorrhoeae* genomic clone shown in FIG. 13 and (b) a second segment having a nucleotide sequence complementary to an oligonucleotide unit of a nucleic acid multimer.

Yet another aspect of the invention is a synthetic oligonucleotide useful as a capture probe in a solution-phase sandwich hybridization assay for *N. gonorrhoeae* comprising (a) a first segment having a nucleotide sequence complementary to a segment of the *N. gonorrhoeae* genomic clone shown in FIG. 13 and (b) a second segment having a nucleotide sequence complementary to an oligonucleotide bound to a solid phase.

A further aspect of the invention is a DNA probe for detecting *N. gonorrhoeae* DNA said probe having a nucleotide sequence that is complementary to all or a portion of either strand of the *N. gonorrhoeae* genomic clone shown in FIG. 13.

A further aspect of the invention is a synthetic oligonucleotide useful as an amplifier probe in a sandwich hybridization assay for the 7.3 kb *N. gonorrhoeae* family of plasmids carrying the beta-Lactamase TEM-1 gene or said gene comprising (a) a first segment having a nucleotide sequence complementary to a segment of said plasmid or said gene and (b) a second segment having a nucleotide sequence complementary to an oligonucleotide unit of a nucleic acid multimer.

Another aspect of the invention is a synthetic oligonucleotide useful as a capture probe in a sandwich hybridization assay for the 7.3 kb *N. gonorrhoeae* family of plasmids carrying the beta-Lactamase TEM-1 gene or said gene comprising (a) a first segment having a nucleotide sequence complementary to a segment of said plasmid or said gene and (b) a second segment having a nucleotide sequence complementary to an oligonucleotide bound to a solid phase.

Another aspect of the invention is a synthetic oligonucleotide useful as a capture probe in a sandwich hybridization assay for the tetM gene in a tetracycline resistant-organism comprising (a) a first segment having a nucleotide sequence complementary to a segment the tetM gene and (b) a second segment having a nucleotide sequence complementary to an oligonucleotide bound to a solid phase.

A further aspect of the invention is a synthetic oligonucleotide useful as an amplifier probe in a sandwich hybridization assay for the tetM gene in a tetracycline resistant organism comprising (a) a first segment having a nucleotide sequence complementary to a segment of the tetM gene and (b) a second segment having a nucleotide sequence complementary to an oligonucleotide unit of a nucleic acid multimer.

Still another aspect of the invention is a synthetic oligonucleotide useful as an amplifier probe in a solution-phase sandwich hybridization assay for *Chlamydia trachomatis* comprising (a) a first segment having a nucleotide sequence complementary to a segment of the Chlamydia pCHL2 plasmid and (b) a second segment having a nucleotide sequence complementary to an oligonucleotide unit of a nucleic acid multimer.

Yet another aspect of the invention is a synthetic oligonucleotide useful as a capture probe in a solution-phase sandwich hybridization assay for *Chlamydia trachomatis* comprising (a) a first segment having a nucleotide sequence complementary to a segment of the Chlamydia pCHL2 plasmid and (b) a second segment having a nucleotide sequence complementary to an oligonucleotide bound to a solid phase.

Still another aspect of the invention is a solution sandwich DNA hybridization for detecting HBV DNA in an analyte comprising:

(a) contacting the analyte under hybridizing conditions with an excess of i) an amplifier probe oligonucleotide comprising a first segment having a nucleotide sequence complementary to a segment of the HBV genome and a second segment having a nucleotide sequence complementary to an oligonucleotide unit of a nucleic acid multimer and (ii) a capture probe oligonucleotide comprising a first segment having a nucleotide sequence complementary to a segment of the HBV genome and a second segment having a nucleotide sequence complementary to an oligonucleotide bound to a solid phase;

(b) contacting under hybridizing conditions the product of step (a) with the oligonucleotide bound to the solid phase;

(c) thereafter separating materials not bound to the solid phase;

(d) contacting under hybridizing conditions the solid phase complex product of step (c) with the nucleic acid multimer, said multimer comprising (i) at least one oligonucleotide unit that is complementary to the second segment of the amplifier probe oligonucleotide and (ii) a multiplicity of second oligonucleotide units that are complementary to a labeled oligonucleotide;

(e) removing unbound multimer;

(f) contacting under hybridizing conditions the solid phase complex product of step (e) with the labeled oligonucleotide;

(g) removing unbound labeled oligonucleotide; and (h) detecting the presence of label in the solid phase complex product of step (g).

Still another aspect of the invention is a solution sandwich DNA hybridization for detecting *N. gonorrhoeae* pilin DNA in an analyte comprising:

(a) contacting the analyte under hybridizing conditions with an excess of (i) an amplifier probe oligonucleotide comprising a first segment having a nucleotide sequence complementary to a segment of *N. gonorrhoeae* pilin DNA genome and a second segment having a nucleotide sequence complementary to an oligonucleotide unit of a-nucleic acid multimer and (ii) a capture probe oligonucleotide comprising a first segment having a nucleotide sequence complementary to a segment of *N. gonorrhoeae* pilin DNA and a second segment having a nucleotide sequence complementary to an oligonucleotide bound to a solid phase;

(b) contacting under hybridizing conditions the product of step (a) with the oligonucleotide bound to the solid phase;

(c) thereafter separating materials not bound to the solid phase;

(d) contacting under hybridizing conditions the solid phase complex product of step (c) with the nucleic acid multimer, said multimer comprising (i) at least one oligonucleotide unit that is complementary to the second segment of the amplifier probe oligonucleotide and (ii) a multiplicity of second oligonucleotide units that are complementary to a labeled oligonucleotide;

(e) removing unbound multimer;

(f) contacting under hybridizing conditions the solid phase complex product of step (e) with the labeled oligonucleotide;

(g) removing unbound labeled oligonucleotide; and (h) detecting the presence of label in the solid phase complex product of step (g).

Still another aspect of the invention is a solution sandwich DNA hybridization for detecting *N. gonorrhoeae* DNA in an analyte comprising:

(a) contacting the analyte under hybridizing conditions with an excess of (i) an amplifier probe oligonucleotide comprising a first segment having a nucleotide sequence complementary to a segment of the *N. gonorrhoeae* genomic clone shown in FIG. 14 and a second segment having a nucleotide sequence complementary to an oligonucleotide unit of a nucleic acid multimer and (ii) a capture probe oligonucleotide comprising a first segment having a nucleotide sequence complementary to a segment of the *N. gonorrhoeae* genomic clone shown in FIG. 14 and a second segment having a nucleotide sequence complementary to an oligonucleotide bound to a solid phase;

(b) contacting under hybridizing conditions the product of step (a) with the oligonucleotide bound to the solid phase;

(c) thereafter separating materials not bound to the solid phase;

(d) contacting under hybridizing conditions the solid phase complex product of step (c) with the nucleic acid multimer, said multimer comprising (i) at least one oligonucleotide unit that is complementary to the second segment of the amplifier probe oligonucleotide and (ii) a multiplicity of second oligonucleotide units that are complementary to a labeled oligonucleotide;

(e) removing unbound multimer;

(f) contacting under hybridizing conditions the solid phase complex product of step (e) with the labeled oligonucleotide;

(g) removing unbound labeled oligonucleotide; and (h) detecting the presence of label in the solid phase complex product of step (g).

Another aspect of the invention is a DNA hybridization assay for detecting *N. gonorrhoeae* DNA in an analyte comprising contacting the analyte under hybridizing conditions with a DNA probe that is complementary to all or a portion of either strand of the *N. gonorrhoeae* genomic clone shown in FIG. 14 and detecting the presence of duplexes containing the DNA probe.

Still another aspect of the invention is a solution sandwich DNA hybridization for detecting *Chlamydia trachomatic* DNA in an analyte comprising:

(a) contacting the analyte under hybridizing condition with an excess of i) an amplifier probe oligonucleotide comprising a first segment having a nucleotide sequence complementary to a segment of the Chlamydia pCHL2 plasmid and a second segment having a nucleotide sequence complementary to an oligonucleotide unit of a nucleic acid multimer and (ii) a capture probe oligonucleotide comprising a first segment having a nucleotide sequence complementary to a segment of the Chlamydia pCHL2 plasmid and a second segment having a nucleotide sequence complementary to an oligonucleotide bound to a solid phase;

(b) contacting under hybridizing conditions the product of step (a) with the oligonucleotide bound to the solid phase;

(c) thereafter separating materials not bound to the solid phase;

(d) contacting under hybridizing conditions the solid phase complex product of step (c) with the nucleic acid multimer, said multimer comprising (i) at least one oligonucleotide unit that is complementary to the second oligonucleotide unit that is complementary to the second segment of the amplifier probe oligonucleotide and (ii) a multiplicity of second oligonucleotide units that are complementary to a labeled oligonucleotide;

(e) removing unbound multimer;

(f) contacting under hybridizing conditions the solid phase complex product of step (e) with the labeled oligonucleotide;

(g) removing unbound labeled oligonucleotide; and (h) detecting the presence of label in the solid phase complex product of step (g).

Still another aspect of the invention is a solution sandwich nucleic acid hybridization assay for detecting a first nucleic acid sequence that is part of a nucleic acid segment that includes a second nucleic acid sequence in a sample that contains said segment and another nucleic acid segment that comprises the first nucleic acid sequence but does not include the second nucleic acid sequence comprising:

(a) contacting the analyte under hybridizing conditions with an excess of (i) an amplifier probe oligonucleotide comprising a first segment that is complementary to one of the first nucleic acid sequence or the second nucleic acid sequence and a second segment that is complementary to an oligonucleotide unit of a nucleic acid multimer and (ii) a capture probe oligonucleotide comprising a first segment that is complementary to the other of the first nucleic acid sequence or the second nucleic acid sequence and a second segment that is complementary to an oligonucleotide bound to a solid phase;

(b) contacting under hybridizing conditions the product of step (a) with the oligonucleotide bound to the solid phase;

(c) thereafter separating materials not bound to the solid phase;

(d) contacting under hybridizing conditions the solid phase complex product of step (c) with the nucleic acid multimer, said multimer comprising (i) at least one oligonucleotide unit that is complementary to the second segment of the amplifier probe oligonucleotide and (ii) a multiplicity of second oligonucleotide units that are complementary to a labeled oligonucleotide;

(e) removing unbound multimer;

(f) contacting under hybridizing conditions the solid phase complex product of step (e) with the labeled oligonucleotide;

(g) removing unbound labeled oligonucleotide; and (h) detecting the presence of label in the solid phase complex product of step (g).

Yet another aspect of the invention is a solution sandwich DNA hybridization for detecting the 7.3 kb *N. gonorrhoeae* plasmid carrying the beta-Lactamase TEM-1 gene or said gene in an analyte comprising:

(a) contacting the analyte under hybridizing conditions with an excess of i) an amplifier probe oligonucleotide comprising a first segment having a nucleotide sequence complementary to a segment of said plasmid or said gene and a second segment having a nucleotide sequence complementary to an oligonucleotide unit of a nucleic acid multimer and (ii) a capture probe oligonucleotide comprising a first segment having a nucleotide sequence complementary to another segment of said plasmid or said gene and a second segment having a nucleotide sequence complementary to an oligonucleotide bound to a solid phase;

(b) contacting under hybridizing conditions the product of step (a) with the oligonucleotide bound to the solid phase;

(c) thereafter separating materials not bound to the solid phase;

(d) contacting under hybridizing conditions the solid phase complex product of step (c) with the nucleic acid multimer, said multimer comprising (i) at least one oligonucleotide unit that is complementary to the second segment of the amplifier probe oligonucleotide and (ii) a multiplicity of second oligonucleotide units that are complementary to a labeled oligonucleotide;

(e) removing unbound multimer;

(f) contacting under hybridizing conditions the solid phase complex product of step (e) with the labeled oligonucleotide;

(g) removing unbound labeled oligonucleotide; and (h) detecting the presence of label in the solid phase complex product of step (g).

Yet another aspect of the invention is a solution sandwich DNA hybridization for detecting tetM gene DNA suspected of containing DNA of a tetracycline resistant organism in an analyte comprising:

(a) contacting the analyte under hybridizing conditions with an excess of i) an amplifier probe oligonucleotide comprising a first segment having a nucleotide sequence complementary to a segment of the tetM gene and a second segment having a nucleotide sequence complementary to an oligonucleotide unit of a nucleic acid multimer and (ii) a capture probe oligonucleotide comprising a first segment having a nucleotide sequence complementary to another segment of said tetM gene and a second segment having a nucleotide sequence complementary to an oligonucleotide bound to a solid phase;

(b) contacting under hybridizing conditions the product of step (a) with the oligonucleotide bound to the solid phase;

(c) thereafter separating materials not bound to the solid phase;

(d) contacting under hybridizing conditions the solid phase complex product of step (c) with the nucleic acid multimer, said multimer comprising (i) at least one oligonucleotide unit that is complementary to the second segment of the amplifier probe oligonucleotide and (ii) a multiplicity of second oligonucleotide units that are complementary to a labeled oligonucleotide;

(e) removing unbound multimer;

(f) contacting under hybridizing conditions the solid phase complex product of step (e) with the labeled oligonucleotide;

(g) removing unbound labeled oligonucleotide; and (h) detecting the presence of label in the solid phase complex product of step (g).

BRIEF DESCRIPTION OF THE DRAWINGS

FIG. 10 shows the DNA sequence of the coding strand of a portion of a 7.3 kb $N.$ $gonorrhoeae$ plasmid carrying the beta-Lactamase TEM-1 gene.

FIG. 11 shows partial nucleotide sequences of the capture and amplifier probes used in the TEM-1NH assay described in Example 6.

FIG. 12 shows partial nucleotide sequences of the capture and amplifier probes used in the TEM-1 assay described in Example 6.

FIG. 13 shows the nucleotide sequence for the tetM gene and partial nucleotide sequences (the 5, ends) of the capture and amplifier probes used in the tetM assay described in Example 8.

FIG. 14 is the DNA sequence of the $N.$ $gonorrhoeae$ genomic sequence SSJK1 described in Example 9.

FIG. 15 shows partial nucleotide sequences of the capture and amplifier probes used in the $N.$ $qonorrhoeae$ assay described in Example 9.

FIG. 16 shows partial nucleotide sequences of the capture and amplifier probes used in the HBV assay described on Example 10.

MODES FOR CARRYING OUT THE INVENTION

Description of Multimers

Figure 1:
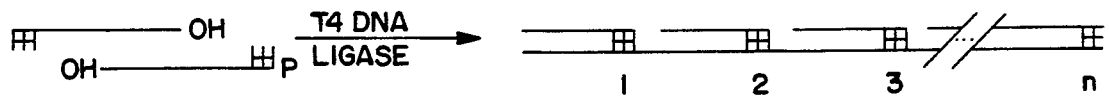
FIG. 1 is a schematic representation of the process for the enzymatic preparation of a linear nucleic acid multimer that is described in Example 1.

The nucleic acid multimers of the invention are linear or branched polymers of the same repeating single-stranded oligonucleotide unit or different single-stranded oligonucleotide units. At least one of the units has a sequence, length, and composition that permits it to bind specifically to a first single-stranded nucleotide sequence of interest, typically analyte or an oligonucleotide bound to the analyte. In order to achieve such specificity and stability, this unit will normally be 15 to 50, preferably 15 to 30, nucleotides in length and have a GC content in the range of 40% to 60%. In addition to such unit(s), the multimer includes a multiplicity of units that are capable of hybridizing specifically and stably to a second single-stranded nucleotide of interest, typically a labeled oligonucleotide or another multimer. These units will also normally be 15 to 50, preferably 15 to 30, nucleotides in length and have a GC content in the range of 40% to 60%. When a multimer is designed to be hybridized to another multimer, the first and second oligonucleotide units are heterogeneous (different).

The total number of oligonucleotide units in the multimer will usually be in the range of 3 to 50, more usually 10 to 20. In multimers in which the unit that hybridizes to the nucleotide sequence of interest is different from the unit that hybridizes to the labeled oligonucleotide, the number ratio of the latter to the former will usually be 2:1 to 30:1, more usually 5:1 to 20:1, and-preferably 10:1 to 15:1.

The oligonucleotide units of the multimer may be composed of RNA, DNA, modified nucleotides or combinations thereof.

The oligonucleotide units of the multimer may be covalently linked directly to each other through phosphodiester bonds or through interposed linking agents such as nucleic acid, amino acid, carbohydrate or polyol bridges, or through other cross-linking agents that are capable of cross-linking nucleic acid or modified nucleic acid strands. The site(s) of linkage may be at the ends of the unit (in either normal 3,-5' orientation or randomly oriented) and/or at one or more internal nucleotides in the strand. In linear multimers the individual units are linked end-to-end to form a linear polymer. In one type of branched multimer three or more oligonucleotide units emanate from a point of origin to form a branched structure. The point of origin may be another oligonucleotide unit or a multifunctional molecule to which at least three units can be covalently bound. In another type, there is an oligonucleotide unit backbone with one or more pendant oligonucleotide units. These latter-type multimers are "fork-like", "comb-like" or combination "fork-" and "comb-like" in structure. The pendant units will normally depend from a modified nucleotide or other organic moiety having appropriate functional groups to which oligonucleotides may be conjugated or otherwise attached. The multimer may be totally linear, totally branched, or a combination of linear and branched portions. Preferably there will be at least two branch points in the multimer, more preferably at least 3, preferably 5 to 10. The multimer may include one or more segments of double-stranded sequences.

Synthesis of Multimers

The multimers may be prepared by cloning (if linear), enzymatic assembly, chemical cross-linking techniques, direct chemical synthesis or a combination thereof. In the case of linear multimers prepared by cloning, nucleic acid sequences that encode the entire multimer or fragments thereof can be made in single- or double-stranded form by conventional cloning procedures. When made in double-stranded form, the multimers/fragments are ultimately denatured to provide single-stranded multimers/fragments. Multimers may be cloned in single-stranded form using conventional single-stranded phage vectors such as M13. Fragments can be linked enzymatically or chemically to form the multimer. When assembled enzymatically, the individual units are ligated with a ligase such as T4 DNA or RNA ligase, as the case may be. When prepared by chemical cross-linking, the individual units may be synthesized with one or more nucleic acids that have been derivatized to have functional groups that provide linking sites or derivatized after the oligonucleotide has been synthesized to provide such sites. A preferred procedure for chemical cross-linking is to incorporate $N^4$-modified cytosine bases into the nucleotide as described in commonly owned copending U.S. application Ser. No. 945,876 filed Dec. 23, 1986, the disclosure of which is incorporated herein by reference.

When prepared by direct chemical synthesis oligonucleotides containing derivatized nucleic acids or equivalent multifunctional molecules whose functional groups are blocked are made by conventional oligonucleotide synthesis techniques. The functional groups are unblocked and oligonucleotide units are synthesized out from the unblocked site(s).

Figure 3:
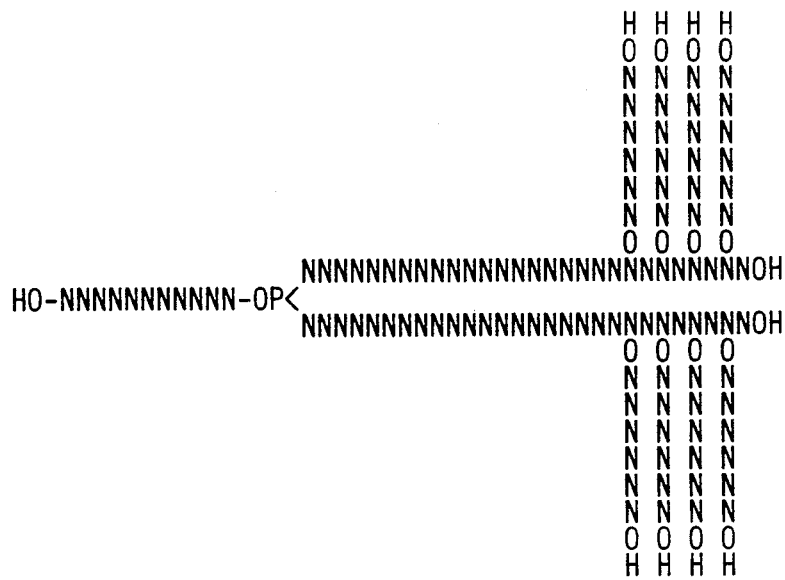
FIG. 3 (Parts A-F), illustrate procedures used in making multimers having "comb-like" and/or bifurcated structures.
Figure 3:
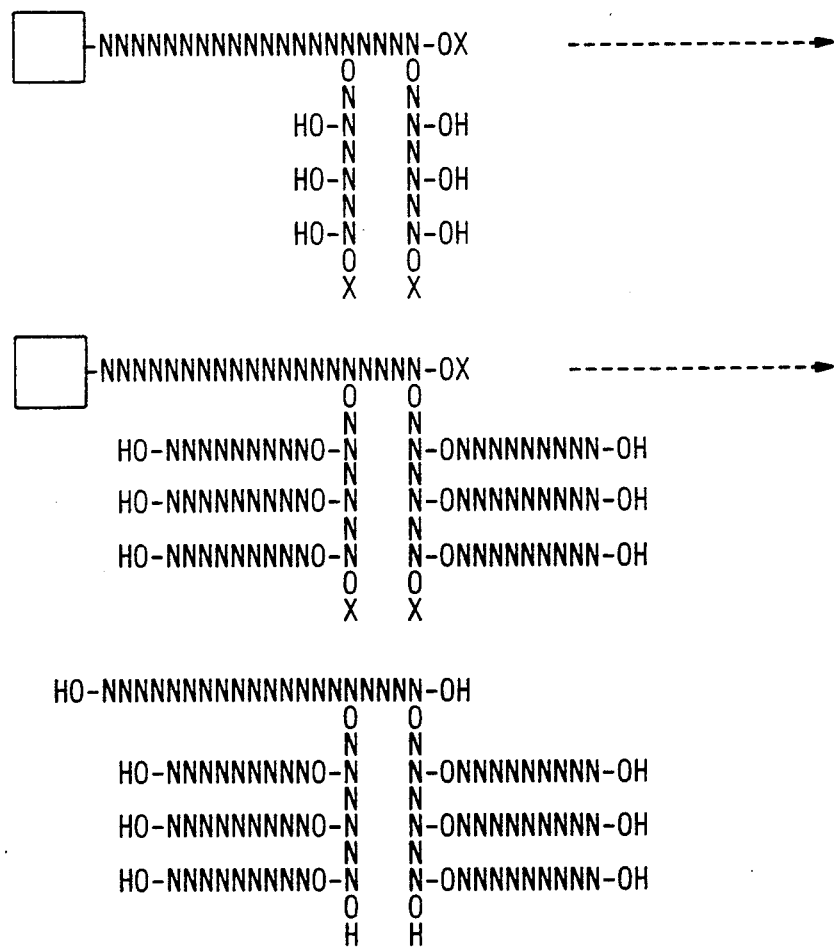

A generic structure for the molecules used to generate branch points in the multimers is as follows:

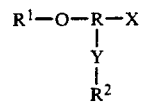
(1)

where R is an organic moiety, preferably a nucleic acid, $R^1$ is a hydroxyl protecting group that can be removed under conditions that do not remove synthetic nucleic acid from a solid phase and do not remove exocyclic nitrogen or phosphate protecting groups, X is a phosphorus-containing group that facilitates nucleic acid synthesis, such as a protected phosphoramidite, phosphonate or phosphate group, Y is a radical derived from a nucleophilic group such as an amino, hydroxyl, sulfhydryl or protected phosphate, and $R^2$ is $R^1$ or a blocking or protective group that can be removed and replaced with hydrogen without affecting $R^1$ In molecules used to generate bifurcated or "fork-like" branching, $R^1$ and $R^2$ are the same; whereas in molecules used to generate "comb-like" branching, $R^2$ is a blocking group that is stable in the presence of an $R^1$ deblocking reagent. FIG. 3 schematically illustrates the procedures used to synthesize multimers having "comb-like" branches, "fork-like" branches, or combinations thereof.

Part A of FIG. 3 depicts a conventional oligonucleotide synthesis scheme for preparing a linear oligonucleotide, such as the automated phosphoramidite method (Warner et al., DNA (1984) 3:401). The dark block represents a solid support, N represents a nucleotide and p-N—$OR_1$ ($R_1$ is equivalent to $R^1$ below), a conventional nucleotide derivative having appropriate protecting groups.

Part B shows the procedure for making a comb-like multimer. The compound

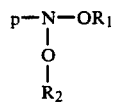

represents a modified base of formula (2) below. An oligomer unit of desired size and sequence is synthesized and left on the support. One or more $N^4$-modified cytosine bases are then incorporated into the chain by said automated procedure. Preferably, the modified base has the formula

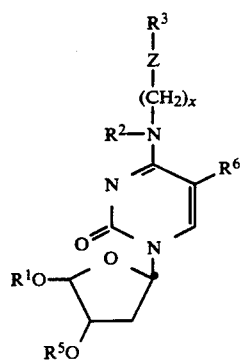
(2)

where Z is a nucleophile such as —O—, —NH—, —S—, $PO_4=$, and

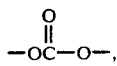

R¹ is a blocking or protective group such as dimethoxytrityl (DMT) or pixyl that is generally base-stable and acid sensitive, R² is hydrogen or methyl, R³ is a blocking or protective group that can be removed and replaced with hydrogen without affecting R¹ such as

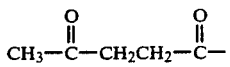

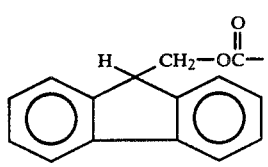

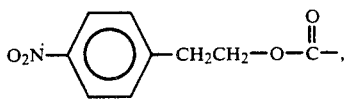

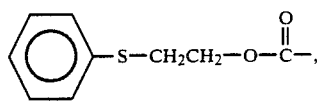

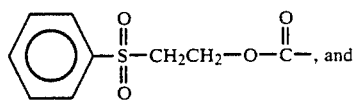

$CH_3O-CH_2-CH_2-O-CH_2-$,

R⁵ is a phosphoramidite or other phosphorus derivative that enables addition of nucletides to the 5' position of an oligonucleotide chain during chemical synthesis (e.g., a phosphodiester, phophotriester, etc.), R⁶ is methyl, hydrogen, I, Br, or F, and X is an integer in the range of 1 to 8, inclusive. When more than one modified base is incorporated they are preferably by a —TT— dimer. Additional oligonucleotide units may be incorporated into the backbone followed by additional modified bases and so forth.

The N⁴ nucleophile group is then deprotected (R³ is removed) and additional oligonucleotide units are generated therefrom by the automated procedure. Residual R¹ groups at the chain terminii are removed and the branched "comb-like" multimer is cleaved from the support.

Part C of FIG. 3 depicts the general procedure for making "fork-like" multimers. Again, an oligomer unit of desired size and sequence is synthesized by conventional techniques and left on the support. A blocked, bifunctional phosphorus-containing group (represented as XP in Part C) such as a blocked phosphoramidite, is then incorporated into the chain by the automated procedure. Preferred bifunctional phosphorus-containing groups are blocked phosphoramidites of the formula

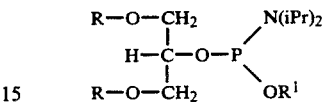

where R is said hydroxyl protecting group, iPr is isopropyl, and R¹ is methyl or beta-cyanoethyl. Most preferably R is DMT and R¹ is beta-cyanoethyl.

Alternatively, the N⁴-modified cytosine base where R₁=R₂ (e.g., DMT) can be used.

The two protecting groups are then removed and additional oligonucleotide units are generated therefrom by the automated procedure. Residual R¹ groups are removed and the bifurcated multimer is cleaved from the support.

Parts D and E depict procedures where two or more bifurcated multimers, "comb-like" multimers or combinations thereof are spliced together enzymatically or chemically. Generally, the bifurcated and/or "comb-like" multimers are prepared as above and removed from the support. They are then combined in solution using the enzymatic or chemical linkage procedures described above.

Part F shows the procedure for synthesizing a multiple "comb-like" multimer. This procedure is a variation of the procedure shown in Part B and involves incorporating modified bases in the dependent side chains and generating secondary oligonucleotide side chains therefrom.

Suitable cleavable linker molecules may be incorporated into the multimers at predetermined sites for the purpose of analyzing the structure of the multimer or as a means for releasing predetermined segments (such as the portion of the multimer that binds to the labeled oligonucleotide). Subsequent to multimer synthesis and purification these linkers can be cleaved specifically without additional degradation of the nucleotide structure of the multimer. A preferred type of linker molecule was designed to contain a 1,2-diol group (which can be cleaved selectively by periodates) as well as a protected hydroxyl and phosphoramidite derived hydroxyl group to permit the linker to be incorporated into any DNA fragment by standard phosphoramidite chemistry protocols. A preferred embodiment of such a linker is the compound:

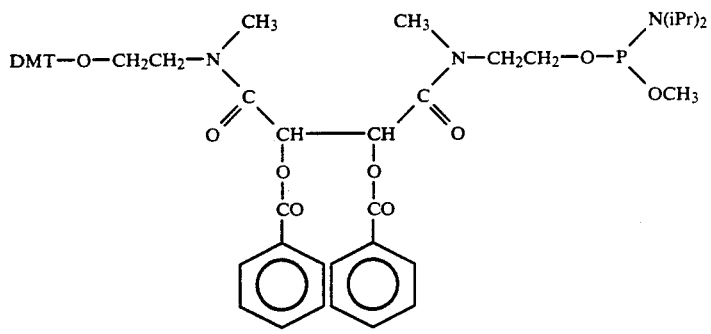

where DMT and iPr are as defined previously. After incorporation into a DNA fragment and complete deprotection the linker-containing fragment has the following structure:

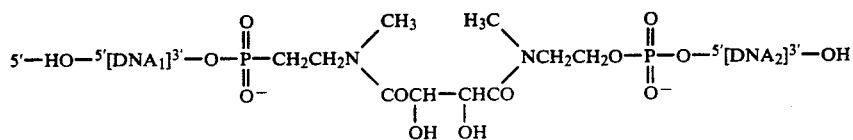

where $DNA_1$ and $DNA_2$ represent DNA subfragments which may be the same- or different. Reaction of this fragment with sodium periodate cleaves the fragment into the following subfragments:

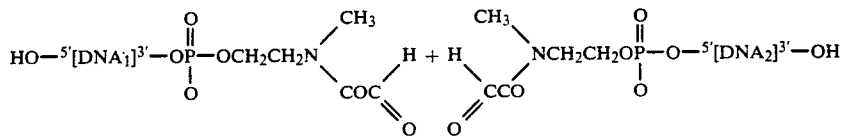

Alternatively, the 1,2-diol group may be replaced with linker groups that contain a hydroxylamine-sensitive linkage, a base-sensitive sulfone linkage, or a thiol-sensitive disulfide linkage. Such linker groups may be derived from conventional cross-linking agents that are used to conjugate proteins to other entities. Likewise, protecting groups other than DMT may be used.

Hybridization Assays

In nucleic acid hybridization assays, the multimer of the invention is bound to the analyte nucleic acid or to a single-stranded oligonucleotide bound to the analyte. Since the multimer includes a relatively large number of oligonucleotide units that are available for binding with the labeled oligonucleotide, many more label groups may be bound to the analyte than in prior procedures. The large number of label groups decreases the threshold level of detectable analyte, in some instances to the subattomole ($10^{-18}$ mole) level.

The multimers may be used in essentially any of the known nucleic acid hybridization formats, such as those in which the analyte is bound directly to a solid phase or sandwich hybridizations in which the analyte is bound to an oligonucleotide that is in turn bound to a solid phase. It is particularly useful in the solution phase sandwich hybridization assay format described in copending application Ser. No. 807,624, filed Dec. 11, 1985.

In a solution-phase sandwich hybridization assay with a capture step the amplifier is used as follows. Single-stranded analyte nucleic acid is incubated under hybridization conditions with an excess of two single-stranded nucleic acid probes (or probe sets), (1) a capture probe having a first binding sequence complementary to the analyte and a second binding sequence that is complementary to a single-stranded oligonucleotide bound to a solid phase, and (2) an amplifier probe having a first binding sequence that is complementary to the analyte and a second binding sequence that is complementary to an oligonucleotide unit of the amplification multimer. By using an amplifier probe, the multimer may be designed to be a "universal" reagent and different multimers need not be made for each analyte. The resulting product is a three component nucleic acid complex of the two probes hybridized to the analyte by their first binding sequences. The second binding sequences of the probes remain as single-stranded tails as they are not complementary to the analyte. Multiple probes of each type may be used.

This complex is then added under hybridizing conditions to a solid phase having a single-stranded oligonucleotide bound to it that is complementary to the second binding sequence of the capture probe. The resulting product comprises the complex bound to the solid phase via the duplex formed by the oligonucleotide bound to the solid phase and the second binding sequence of the capture probe. The solid phase with bound complex is then separated from unbound materials.

The multimer is then added to the solid phase-analyte-probe complex under hybridization conditions to permit the multimer to hybridize to the available second binding sequences of the amplifier probe of the complex. The resulting solid phase complex is then separated from any unbound multimer by washing. The labeled oligonucleotide is then added under conditions which permit it to hybridize to the complementary oligonucleotide units of the multimer. The resulting solid phase labeled nucleic acid complex is then separated from excess labeled oligonucleotide, by washing to remove unbound labeled oligonucleotide, and read.

The amplification may be multiplied by the use of more than one multimer in the assay. In such instances a first multimer is designed to function as or to bind to the amplifier probe and to a second multimer and the second multimer is designed to bind to the first multimer and to the labeled oligonucleotide. Any number of multimers may be bound in series in this manner to achieve even greater amplification.

The analyte nucleic acids may be from a variety of sources, e.g., biological fluids or solids, food stuffs, environmental materials, etc., and may be prepared for the hybridization analysis by a variety of means, e.g., proteinase K/SDS, chaotropic salts, etc. Also, it may be of advantage to decrease the average size of the analyte nucleic acids by enzymatic, physical or chemical means, e.g., restriction enzymes, sonication, chemical degradation (e.g., metal ions), etc. The fragments may be as small as 0.1 kb, usually being at least about 0.5 kb and may be 1 kb or higher. The analyte sequence is provided in single-stranded form for analysis. Where the sequence is naturally present in single-stranded form, denaturation will not be required. However, where the sequence is present in double-stranded form, the sequence will be denatured. Denaturation can be carried out by various techniques, such as alkali, generally from about 0.05 to 0.2 M hydroxide, formamide, salts, heat, or combinations thereof.

The first binding sequences of the capture probe and amplifier probe that are complementary to the analyte sequence will each be of at least 15 nucleotides (nt), usually at least 25 nt, and not more than about 5 kb, usually not more than about 1 kb, preferably not more than about 100 nt. They will typically be approximately 30 nt. They will normally be chosen to bind to different sequences of the analyte. The first binding sequences may be selected based on a variety of considerations. Depending upon the nature of the analyte, one may be interested in a consensus sequence, a sequence associated with polymorphisms, a particular phenotype or genotype, a particular strain, or the like.

By appropriate selection of the first binding sequences of the amplifier and capture probes they may be used to identify a specific nucleic acid molecule that includes a particular gene or other sequence that is present as part of different nucleic acid molecules. In order to discriminate the nucleic acid molecule of interest from other molecules that also contain the given sequence, one of the probes is made complementary to the given sequence while the other is made complementary to another sequence of the molecule which other sequence is unique to that molecule (i.e., is not present in the other molecules that contain the given sequence). Such a technique is exemplified by the TEM-1NH assay described in the examples, infra.

The second binding sequences of the capture probe and amplifier probe are selected to be complementary, respectively, to the oligonucleotide attached to the solid phase and to an oligonucleotide unit of the multimer and so as to not be encountered by endogenous sequences in the sample/analyte. The second binding sequence may be contiguous to the first binding sequence or be spaced therefrom by an intermediate noncomplementary sequence. The probes may include other noncomplementary sequences if desired. These noncomplementary sequences must not hinder the binding of the binding sequences or cause nonspecific binding to occur.

The capture probe and amplifier probe may be prepared by oligonucleotide synthesis procedures or by cloning, preferably the former.

It will be appreciated that the binding sequences need not have perfect complementarity to provide homoduplexes. In many situations, heteroduplexes will suffice where fewer than about 10% of the bases are mismatches, ignoring loops of five or more nucleotides. Accordingly, as used herein the term "complementary" intends a degree of complementarity sufficient to provide a stable duplex structure.

The solid phase that is used in the assay may be particulate or be the solid wall surface of any of a variety of containers, e.g., centrifugal tubes, columns, microtiter plate wells, filters, tubing, etc. When particles are used, they will preferably be of a size in the range of about 0.4 to 200 microns, more usually from about 0.8 to 4.0 microns. The particles may be any convenient material, such as latex, or glass. Microtiter plates are a preferred solid surface. The oligonucleotide that is complementary to the second binding sequence of the capture probe may be stably attached to the solid surface through functional groups by known procedures.

It will be appreciated that one can replace the second binding sequence of the capture probe and the oligonucleotide attached to the solid phase with an appropriate ligand-receptor pair that will form a stable bond joining the solid phase to the first binding sequence of the capture probe. Examples of such pairs are biotin/avidin, thyroxine/thyroxine-binding globulin, antigen/antibody, carbohydrate/lectin, and the like.

The labeled oligonucleotide will include a sequence complementary to the second oligonucleotide units of the multimer. The labeled oligonucleotide will include one or more molecules ("labels"), which directly or indirectly provide for a detectable signal. The labels may be bound to individual members of the complementary sequence or may be present as a terminal member or terminal tail having a plurality of labels. Various means for providing labels bound to the sequence have been reported in the literature. See, for example, Leary et al., *Proc Natl Acad Sci USA* (1983) 80:4045; Renz and Kurz, *Nucl Acids Res* (1984) 12:3435; Richardson and Gumport, *Nucl Acids Res* (1983) 11:6167; Smith et al., *Nucl Acids Res* (1985) 13:2399; Meinkoth and Wahl, *Anal Biochem* (1984) 138:267. The labels may be bound either covalently or non-covalently to the complementary sequence. Labels which may be employed include radionuclides, fluorescers, chemiluminescers, dyes, enzymes, enzyme substrates, enzyme cofactors, enzyme inhibitors, enzyme subunits, metal ions, and the like. Illustrative specific labels include fluorescein, rhodamine, Texas red, phycoerythrin, umbelliferone, luminol, NADPH, $\alpha$-,$\beta$-galactosidase, horseradish peroxidase, etc.

The labeled oligonucleotide can be conveniently prepared by chemical synthesis such as that described in commonly owned copending application Ser. No. 945,876. By providing for a terminal group which has a convenient functionality, various labels may be joined through the functionality. Thus, one can provide for a carboxy, thiol, amine, hydrazine or other functionality to which the various labels may be joined without detrimentally affecting duplex formation with the sequence. As already indicated, one can have a molecule with a plurality of labels joined to the sequence complementary to the labeling sequence. Alternatively, one may have a ligand bound to the labeling sequence and use a labeled receptor for binding to the ligand to provide the labeled analyte complex.

The ratio of capture probe and amplifier probe to anticipated moles of analyte will each be at least stoichiometric and preferably in excess. This ratio is preferably at least about 1.5:1, and more preferably at least 2:1. It will normally be in the range of 2:1 to 10,000:1. Concentrations of each of the probes will generally range from about $10^{-9}$ to $10^{-6}$ M, with sample nucleic acid concentrations varying from $10^{-21}$ to $10^{-12}$ M. The hybridization steps of the assay will generally take from about 10 minutes to 2 hours, frequently being completed in about 1 hour. Hybridization can be carried out at a mildly elevated temperature, generally in the range from about 20° C. to 80° C., more usually from about 35° C. to 70° C., particularly 65° C.

The hybridization reaction is usually done in an aqueous medium, particularly a buffered aqueous medium, which may include various additives. Additives which may be employed include low concentrations of detergent (0.1 to 1%), salts, e.g., sodium citrate (0.017 to 0.170 M), Ficoll, polyvinylpyrrolidine, carrier nucleic acids, carrier proteins, etc. Nonaqueous solvents may be added to the aqueous medium, such as dimethylformamide, dimethylsulfoxide, alcohols, and formamide. These other solvents will be present in amounts ranging from 2 to 50%.

The stringency of the hybridization medium may be controlled by temperature, salt concentration, solvent system, and the like. Thus, depending upon the length and nature of the sequence of interest, the stringency will be varied.

The procedure used in the separation steps of the assay will vary depending upon the nature of the solid phase. For particles, centrifugation or filtration will provide for separation of the particles, discarding the supernatant or isolating the supernatant. Where the particles are assayed, the particles will be washed thoroughly, usually from one to five times, with an appropriate buffered medium, e.g., PBS containing a detergent-such as SDS. When the separation means is a wall or support, the supernatant may be isolated or discarded and the wall washed in the same manner as indicated for the particles.

Depending upon the nature of the label, various techniques can be employed for detecting the presence of the label. For fluorescers, a large number of different fluorometers are available. For chemiluminescers, luminometers or films are available. With enzymes, a fluorescent, chemiluminiscent, or colored product can be provided and determined fluorometrically, luminometrically, spectrophotometrically or visually. The various labels which have been employed in immunoassays and the techniques applicable to immunoassays can be employed with the subject assays.

In a hybridization assay in which the analyte nucleic acid is bound directly to a solid phase, such as a "dot blot" assay, the multimer is hybridized directly to the bound analyte. In these instances, the first oligonucleotide unit(s) of the multimer is complementary to a sequence of the analyte and the second oligonucleotide units are complementary to a labeled oligonucleotide. Unbound multimer is removed from the solid phase and the labeled oligonucleotide is then hybridized to the bound analyte-multimer complex. Excess labeled oligomer is removed and the labeled, bound complex is read.

The multimers may also be used in other assays such as direct, indirect, and sandwich immunoassays. In these instances the reagent that plays the role of the labeled antibody or other ligand that is bound directly or indirectly to the analyte has an oligonucleotide that is complementary to the first oligonucleotide unit of the multimer bound to it rather than a label. For instance, in a sandwich immunoassay for an antigen analyte, the analyte sample is incubated with a solid phase to which is bound a first antibody to the antigen. Unbound sample is removed from the solid phase and a second antibody to the antigen and which an oligonucleotide complementary to a unit of the multimer is bound is reacted with the bound complex to form a three-membered complex. Following removal of excess second antibody the multimer is then hybridized to the complex via the oligonucleotide bound to the second antibody. Excess multimer is removed and a labeled oligonucleotide is hybridized to the other oligonucleotide units of the multimer. After removal of excess labeled oligonucleotide, the complex is read.

Kits for carrying out amplified nucleic acid hybridization assays according to the invention will comprise in packaged combination the following reagents: the multimer; an appropriate labeled oligonucleotide; a solid phase that is capable of binding to the analyte; optionally a capture probe if the assay format is one in which the analyte is bound to the solid phase through an intermediate oligonucleotide or other ligand; and optionally an amplifier probe if the assay format is one in which the multimer is not hybridized directly to the analyte. These reagents will typically be in separate containers in the kit. The kit may also include a denaturation reagent for denaturing the analyte, hybridization buffers, wash solutions, enzyme substrates, negative and positive controls and written instructions for carrying out the assay.

The following examples of the invention are offered by way of illustration and not by way of limitation.

EXAMPLES

1. Enzymatic Preparation of Linear Multimer A linear multimer of an 18-mer that is complementary to amplifier probes (see 3.F. below) was prepared according to the scheme depicted in FIG. 1.

Two 18-mers, LLA-1 and LLA-2, were synthesized by an automated phosphoramidite method as described in Warner et al., DNA (1984) 3:401. Purification was carried out according to Sanchez-Pescador and Urdea, DNA (1984) 3:339. Phosphorylation of the 5' end of the LLdA-2 was carried out by the chemical phosphorylation procedure described in Example 1 of commonly owned copending U.S. application Ser. No. 087,158, filed Aug. 18, 1987, the disclosure of which is incorporated herein by reference. The sequences of LLA-1 and LLA-2 were as follows.

| | |
|---|---|
| 5'-CGTGTCAGGCATAGGACC | LLA-1 |
| TCCGTATCCTGGGCACAG-p-5' | LLA-2 |

The linear LLA-2 polymer was formed using T4 DNA ligase. The products of such ligations are double-stranded. Single-stranded polymer may be obtained by gel purifying the product under denaturing conditions.

One hundred thousand pmole of each sequence were added to a 1.5 ml tube and evaporated to dryness under vacuum.

The following solution was added to the dried sequences:
100 μl KBTS buffer*
100 μl 10 mM DTT
100 μl 10 mM ATP
50 μl H₂O
50 μl 1 M NaCl
500 μl 30% PEG.
*10×(50 mM Tris HCl, pH 7.6, 10 mM MgCl₂, 1 mg/ml spermidine)

The tube was vortexed and then heated to 55° C. for 30 min. The tube was then cooled to room temperature and the following solution was added
6.7 μl T4 DNA Ligase (New England Nuclear 15 U/μl)
18.8 μl 5×Ligase Dilution Buffer (NEN)
74. 5 μl H₂O Again the tube was vortexed and then incubated at room temperature overnight. The reaction mixture was extracted with n-butanol to a volume of 100 μl, 100 μl of 3×stop mix (25% glycerol, 0.05% bromphenol blue, 0.5% sodium dodecyl sulfate, 25 mM EDTA) was added and then heated to 100° C. for 5 min. to denature the sample. Twenty μl portions of this solution were then added to the wells of a 7% denaturing polyacrylamide gel (10 cm×10 cm×1.5 mm). The gel was run at 10 V/cm until the bromphenol blue dye was within 0.5 cm of the bottom of the gel. The products formed were made visible by placing the gel on a thin layer chromatography plate containing a UV fluorescing dye covered with Saran wrap and illuminating with a long wave UV lamp. The products absorb the UV irradiation and cast a visible shadow. Bands of increasing length were observed and polymeric products greater than twenty oligomeric units long were cut out. These products were eluted from the gel by soaking in Maxim-Gilbert buffer (0.1 M Tris-HCl, pH 8, 0.5 M NaCl, 5 mM EDTA).

2. Chemical Preparation of Linear and Branched Multimers

A. Preparation of Linear and Branched Multimers

Figure 2A:
FIGS. 2A and 2B are schematic representations of the processes for the chemical preparation of linear and branched nucleic acid multimers that are described in Example 2.
Figure 2B:
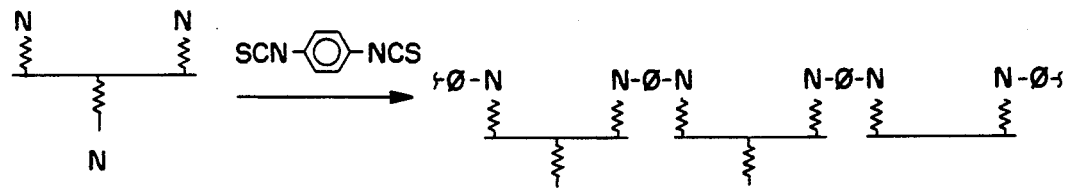
Figure 2B:
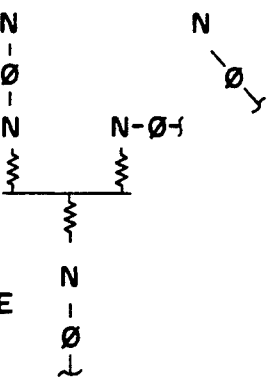

Linear and branched multimers of an 18-mer that are complementary to the amplifier probes (see 3.F. below) were prepared according to the schemes depicted in FIGS. 2A and 2B.

As indicated, the schemes use oligonucleotide units having derivatized bases that are cross-linked with phenyldiisothiocyanate (DITC).

The oligonucleotide used to prepare the linear multimer had the sequence

3'-XGCACAGTCCGTATCCTGGX-5' where X represents the N⁴-(6-aminocaproyl-2-aminoethyl) derivative of cytidine.

The oligonucleotide used for the branched multimer had the sequence

5,-XTGGTCCTATGCCTGACACGTXTGGTC-CTATGCCTGACACGTXT-3' where X is as above.

The N⁴-(6-aminocaproyl-2-aminoethyl) derivative of cytidine was prepared as described in commonly owned copending application Ser. No. 945,876. The oligomers were synthesized and purified as described in Example 1.

A sample of 0.2 OD₂₆₀ units of either fragment was dissolved in 0.5 μl of 0.1 M sodium borate, pH 9.3, to which 9.5 μl of DITC in dimethylformamide (2 mg/ml) was added. The solution was vortexed and set at room temperature overnight in the dark. After the addition of 300 μl of n-butanol and mixing, 300 μl of water was added. The mixture was vortexed and centrifuged to separate the layers. The sample was extracted several times until the aqueous phase was lowered to a volume of approximately 50 μl and then vacuumed to dryness. The polymer was then treated with 10 μl of 1 M glycine, pH 9.5, for 2 hr to modify any remaining isothiocyanate groups. The mixture was loaded onto a 10 ml Sephadex G-25 column, eluted with water, collected, evaporated to dryness, taken up in 1% SDS and loaded onto a 7% polyacrylamide gel (vertical 2% agarose gels are preferred for preparation runs). The gel was run at 60 ma and then stained with ethidium bromide. Bands estimated to comprise 10–25 units of the oligomer were cut, electroeluted and precipitated.

B. Preparation of Comb-like and Bifurcated Multimers

In this section DMT=dimethoxytrityl; T=deoxythymidine; DMF=dimethylformamide; BDMS=t-butyldimethylsilyl; C=deoxycytidine; TLC=thin-layer chromatography; DMAP=N,N-dimethylaminopyridine; THF=tetrahydrofuran; DIPEA=diisopropylethylamine; LEV=levulinic ester; DCA=dichloroacetic acid; DCC=dicyclohexylcarbodiimide; DCHU=dicyclohexylurea; TEA=triethylamine; TMS=trimethylsilyl; FMOC=9-fluorenylmethoxycarbonyl.

B.1A. Synthesis of Nucleotide for Forming Comb-Like Branch Points

5-DMT-T—OH (27.3 g, 50 mmole) and imidazole (10 g, 150 mmole) were coevaporated with 200 ml DMF. The residue was dissolved in 250 ml DMF, and BDMS chloride (75 mmol) was added. The reaction mixture was stirred for 18 hr at 20° C. Methanol (50 ml) was added and after 30 min the solvents were removed in vacuo. The oily residue was dissolved in 50 ml ethyl acetate, and the organic phase extracted with 5% aqueous NaHCO (2×500 ml) and 80% saturated aqueous NaCl (500 ml) and finally dried over solid Na₂SO₄. The solvent was removed in vacuo to give 35 g (50 mmole) 5'-DMT-3'BDMS T (100% yield). This material was used without further purification.

Triazole (25.6 g) was suspended in 400 ml of CH₃CN (at 0° C.) and POCl₃ (8 ml) was added with rapid stirring. Then triethylamine (60 ml) was added dropwise over 15 min to the slurry stirred at 0° C. for 30 min. 5'-DMT-3'BDMS T (25 mmole crude) dissolved in 100 ml CH₃CN was added dropwise to the above stirred slurry at 0° C. The ice-water bath was removed and stirring continued at 20° C. for one hour. The reaction mixture was diluted with 800 ml ethyl acetate, and the organic phase was extracted with NaHCO (2×500 ml) and 80% saturated aqueous NaCl (500 ml). After drying the organic phase over solid Na₂SO₄ solvents were removed in vacuo. The resulting residue was coevaporated with toluene (400 ml) and CH₃CN (400 ml) to give 5'-DMT-3'-BDMS-5-methyl-4-triazoyl β-D-2-deoxyribofuranosyl-2(1H)-pyrimidinone as a white foam in quantitative yield. This material was used without further purification.

To a solution of 6-aminohexanol (11.7 g, 100 mmole) in 400 ml CH CN was added dropwise 5'-DMT-3'-BDMS-5-methyl-4-triazoyl β-D-2-deoxyribofuranosyl-2(1H)-pyrimidinone (8.7 g, 12 mmole) dissolved in 100 ml CH₃CN and the reaction mixture stirred at 20° C. The progress of the reaction was monitored by TLC (every 30 min) and when the starting material had completely disappeared (usually in 1-2 hours), the reaction mixture was diluted with 500 ml ethyl acetate, which was extracted with 5% aqueous NaHCO₃ and 80% saturated aqueous NaCl as described above. After drying of the organic phase over Na₂SO₄, the solvent was removed in vacuo to give 7.0 g (9.2 mmole) of product 5'-DMT-3'-BDMS-5-methyl-N⁴-6-hydroxyhexyl deoxycytidine (yield 77%). This material was used without further purification.

To a solution of 5'-DMT-3'-BDMS-5-methyl-N⁴-6-hydroxyhexyl deoxycytidine (7 g, 9.2 mmole) in 100 ml THF was added (CH₃COCH₂CH₂CO)₂O (50 mmole) dissolved in 100 ml THF and then 10 ml 6.5% DMAP in 2,6-lutidine/THF. The reaction mixture was left stirring for 30 min. The analysis showed that starting material had been completely consumed. The reaction mixture was diluted with 700 ml ethyl acetate which was diluted with 700 ml ethyl acetate which was extracted with 5% aqueous NaHCO (3×500 ml) and 80% saturated aqueous NaCl (500 ml) as described above. After drying over solid Na₂SO₄, the solvent was removed and the residue coevaporated with toluene (200 ml) and CH₃CN (200 ml) to give 12.3 g of crude product.

This crude product was dissolved in 100 ml THF, and 10 ml of a 1.1 M solution of tetrabutylammonium fluoride in THF was added. The progress of the reaction was monitored by TLC; it is usually over in 30 min but may take longer. When starting material had been consumed, the reaction mixture was diluted with 700 ml ethyl acetate, which was extracted with NaHCO₃ and NaCl solutions, as above. Removal of the solvent afforded 8.5 g crude product 5'-DMT-5-methyl-N⁴(O-levulinyl-6-oxyhexyl)-2'-deoxycytidine. This material was subjected to silica gel chromatography. The purified product was isolated by elution with 4% methanol in CH₂Cl₂ to give 5.0 g of a slightly brownish foam (6.7 mmole; 73% yield).

Silica-purified 5'-DMT-5-methyl-N⁴(O-levulinyl-6-oxyhexyl)-2'-deoxycytidine (7.7 mmole) was coevaporated twice with CH₃CN. The resulting dry powder was dissolved in 70 ml CH₂Cl₂ containing 4.9 ml DIPEA in a flask under argon. After cooling to 0° C., 1.65 ml (8.5 mmole) N,N-diisopropylaminomethoxy chlorophosphine was added with a syringe and the mixture stirred at 0° for 30 min. After dilution with 400 ml ethyl acetate, the organic phase was washed 4 times with 400 ml 80% saturated aqueous NaCl, then dried over solid Na₂SO₄ and filtered. The solvent was removed in vacuo and the resulting residue coevaporated twice with toluene to give an oil. This oil was dissolved in 30 ml toluene and added dropwise into 400 ml cold hexane (∼ −20° C.). The precipitate was quickly collected by filtration and dried in vacuo for 18 hr to give 5.45 g of phosphoramidite (6.0 mmole; 78% yield).

B.1B. Synthesis of Alternative, Preferred Nucleotide for Forming Comb-Like Branch Points To a solution of 5'-DMT-3-BDMS-5-methyl-N⁴-6-hydroxyhexyl deoxycytidine (34 g, 50 mmole) prepared as described above in 200 ml CH₂Cl₂ was added 1.5 g N,N-dimethylaminopyridine and 25 ml triethylamine. To this solution at 0° C. was added dropwise DMT-Cl (75 mmole, 25.5 g) dissolved in CH₂Cl₂ (100 ml). The reaction mixture was left stirring for 1 hour. The analysis showed that starting material had been completely consumed. Then 50 ml of methanol was added. After 30 min the reaction mixture was diluted with 800 ml ethyl acetate which was extracted with 5% NaHCO₃ (2×500 ml) and 80% saturated aqueous NaCl (500 ml) described above. After drying over solid Na₂SO₄ the solvent was removed in vacuo and the residue coevaporated with toluene (200 ml) and CH₃CH (200 ml).

This crude product was dissolved in 200 ml THF, and 200 ml of a 1.1 M solution of tetrabutylammonium fluoride in THF was added. The progress of the reaction was monitored by TLC; it is usually over in 30 min but may take longer. When starting material had been consumed, the reaction mixture was diluted with 700 ml ethyl acetate, which was extracted with NaHCO₃ and NaCl solutions, as above. Removal of the solvent afforded 36 g crude product, 5'-DMT-5-methyl-N⁴(O-DMT-6-oxyhexyl)deoxycytidine. This material was subjected to silica gel chromatography. The purified product was isolated by elution with 2–4% methanol in CH₂Cl₂ to give 32.7 g of pure product (34 mmole; yield based on 5'-DMT-T-OH: 69%).

Silica-purified 5'-DMT-5-methyl-N⁴(0-DMT-6-oxyhexyl)-2'-deoxycytidine (34 mmole) was coevaporated twice with CH₃CN. The resulting dry powder was dissolved in 100 ml CH₂Cl₂ containing 7.5 ml DIPEA in a flask under argon. After cooling to 0° C., 7.37 ml (38 mmole) N,N-diisopropylaminomethoxy chlorophosphine was added with a syringe and the mixture stirred at 0° for 30 min. After dilution with 800 ml ethyl acetate, the organic phase was washed 4 times with 800 ml 80% saturated aqueous NaCl, then dried over solid Na₂SO₄ and filtered. The solvent was removed in vacuo and the resulting residue coevaporated twice with toluene to give an oil. This oil was dissolved in 80 ml toluene and added dropwise into 700 ml cold hexane (∼ −20° C.). The precipitate was quickly collected by filtration and dried in vacuo for 18 hr to give 31.8 g of phosphoramidite (28.7 mmole; 84% yield).

5'-DMT-T-OH (16.4, 30 mmole) was dissolved in dry 200 ml CH CN and 1-(TMS)imidazole (14.6 ml, 100 mmole) was added. After 60 min the solvents were removed in vacuo. The oily residue was dissolved in 700 ml ethyl acetate, and the organic phase extracted with 5% aqueous NaHCO₃ (2×500 ml) and 80% saturated aqueous NaCl (500 ml) and finally dried over solid Na₂SO₄. The solvent was removed in vacuo to give 30 mmole 5'-DMT-3'-TMS-T (100% yield). This material was used without further purification.

Triazole (37.8 g) was suspended in 450 ml of CH₃CN (at 0° C.) and POCl₃ (12 ml) was added with rapid stirring. Then triethylamine (90 ml) was added dropwise over 15 min to the slurry stirred at 0° C. for 30 min. 5'-DMT-3'-TMS-T (30 mmole crude) dissolved in 100 ml CH₃CN was added dropwise to the above stirred slurry at 0° C. The ice-water bath was removed and stirring continued at 20° C. for one hour. The reaction mixture was diluted with 800 ml ethyl acetate, and the organic phase was extracted with 5% NaHCO (2×500 ml) and 80% saturated aqueous NaCl (500 ml). After drying the organic phase over solid Na₂SO₄ solvents were removed in vacuo. The resulting residue was coevaporated with toluene (400 ml) and CH₃CN (400 ml) to give 5'-DMT-3'-TMS-5-methyl-4-triazoyl β-D-2-deoxyribofuranosyl-2(1H)-pyrimidinone as a white foam in quantitative yield. This material was used without further purification.

To a solution of 6-aminohexanol (23 g, 200 mmole) in 400 ml CH₃CN was added dropwise 5'-DMT-3'-TMS- 5-methyl-4-triazoyl β-D-2-deoxyribofuranosyl-2(1H)-pyrimidinone (20 g, 30 mmole) dissolved in 100 ml CH₃CN and the reaction mixture stirred at 20° C. The progress of the reaction was monitored by TLC (every 30 min) and when the starting material had completely disappeared (usually in 1-2 hours), the reaction mixture was diluted with 800 ml ethyl acetate, which was extracted with 5% aqueous NaHCO₃ and 80% saturated aqueous NaCl as described above. After drying of the organic phase over Na₂SO₄, the solvent was removed in vacuo to give 20.3 g (~30 mmole) of product 5'-DMT-3'-TMS-5-methyl-N⁴-6-hydroxyhexyl deoxycytidine. This material was used without further purification.

To a solution of 5'-DMT-3'-TMS-5-methyl-N⁴(6-hydroxyhexyl)deoxycytidine in 250 ml methanol was added 25 ml concentrated aqueous NH₄OH and the reaction mixture left stirring in a closed round-bottom flask to 1 hour. The solvent was then removed in vacuo and coevaporated with 1×200 ml ethanol, 1×100 ml toluene and 1×100 ml CH₃CN to give 5'-DMT-5-methyl-N⁴(6-hydroxylhexyl)deoxycytidine in quantitative yield. This material was used without further purification. This material was dissolved in 200 ml CH₂Cl₂ and 4 ml of pyridine was added followed by dropwise addition of FMOC-Cl (7.8 g, 30 mmole) dissolved in CH₂Cl₂ (50 ml). The reaction mixture was left stirring for 30 min. The analysis showed that starting material had been completely consumed. The reaction mixture was diluted with 500 ml ethyl acetate which was extracted with 5% aqueous NaHCO₃ (3×500 ml) and 80% saturated aqueous NaCl (500 ml) as described above. After drying over solid Na₂SO₄, the solvent was removed and the residue coevaporated with toluene (200 ml) and CH₃CN (200 ml) to give 23.7 g of crude product. This crude product was subjected to silica gel chromatography. The purified product eluted with about 4% methanol in CH₂Cl to give 13.3 g (15.3 mmole) of pure 5'-DMT-5-methyl-N⁴(0-FMOC-6-oxyhexyl)deoxycytidine (50% yield based on 5'-DMT-TOH).

Silica-purified 5'-DMT-5-methyl-N⁴(O-FMOC-6-oxyhexyl)-2'-deoxycytidine (15.3 mmole) was coevaporated twice with CH₃CN. The resulting dry powder was dissolved in 60 ml CH₂Cl₂ containing 4.1 ml DIPEA in a flask under argon. After cooling to 0° C., 3.19 ml (16.5 mmole) N,N-diisopropylaminomethoxy chlorophosphine was added with a syringe and the mixture stirred at 0° for 30 min. After dilution with 400 ml ethyl acetate, the organic phase was washed 4 times with 400 ml 80% saturated aqueous NaCl, then dried over solid Na₂SO₄ and filtered. The solvent was removed in vacuo and the resulting residue coevaporated twice with toluene to give an oil. This oil was dissolved in 50 ml toluene and added dropwise into 400 ml cold hexane (~ −20° C.). The precipitate was quickly collected by filtration and dried in vacuo for 18 hr to give 12.15 g of phosphoramidite (11.8 mmole; 77% yield). Removal of 0-FMOC group during solid phase synthesis: t-butylamine/pyridine (1:10 v/v) for 1 hour at 20°. Removal of O-levulinyl group: 0.5 M hydrazine hydrate in pyridine/glacial acetic acid (4:1 v/v) 15 minutes at 20° C.

B.2. Synthesis of a Multifunctional Phosphoramidite for Forming Bifurcated Branch Points Glycerol (10 mmole) was dried by coevaporation with pyridine. The resulting oil was dissolved in 50 ml pyridine and DMT-Cl (6.8 g, 20 mmole) was added, and the reaction mixture was stirred at 20° C. for 18 hr. After addition of methanol (10 ml), the solvent was removed on a rotary evaporator. The resulting oil was dissolved in 250 ml ethyl acetate and the organic phase was washed with 5% aqueous NaHCO₃ (2×250 ml), 80% saturated aqueous NaCl (1×250 ml) and then dried over solid Na₂SO₄. The solvent was removed in vacuo and the residue coevaporated with 100 ml toluene and 100 ml CH₃CN. The product was isolated by silica gel chromatography to give 2.5 g (3.6 mmole) O,O-bis DMT glycerol (35% yield). Product elutes with 0-1% MeOH.

The bis-DMT glycerol (2.3 mmole) was dissolved in CH₂Cl₂ (10 ml) containing DIPEA (0.8 ml) under argon, and N,N-diisopropylamino-2-cyanoethoxy-chlorophosphine (1 ml) was added by syringe. After 30 minutes the mixture was diluted with ethyl acetate (200 ml) and the organic phase washed with 200 ml 80% saturated aqueous NaCl. After drying over solid Na₂SO₄, the solvent was removed in vacuo, and the residue coevaporated with 100 ml toluene yield) of bis-DMT glycerol phosphoramidite. The product was dispensed with dry CH₃CN into small septum-capped vials and after removal of the solvent stored at −20° C. under argon.

B.3. Synthesis of Periodate-Cleavable Linker Phosphoramidite

O,O-Dibenzoyl tartaric acid monohydrate (18.8 g, mmole) was dissolved in 250 ml CH₃CN and the solvent was removed in vacuo. This process was repeated. The resulting oil was dissolved in 250 ml THF and DCC (10.6g, mmole) dissolved in 50 ml THF was added. A precipitate started forming in a few minutes. After stirring for 18 hr at 20° C. the reaction mixture was filtered, and the precipitate washed with THF. The precipitate was dried in high vacuum to give 10.8g (50 mmole) DCHU. To the combined filtrate was added 2-(N-methyl)aminoethanol (4.0 ml, 50 mmole) and the reaction mixture was stirred for 1 hr at 20° C. DCC (10.6g, 50 mmole) in 50 ml THF was then added. A small precipitate formed. After about 1 hr, 2 -(N-methyl)aminoethanol (4.0 ml, 50 mmole) was added and the reaction mixture stirred for 18 hours at 20° C.

The formed precipitate was filtered off and washed with THF. The dried precipitate of DCHU weighed 10.8 g. The combined filtrate was evaporated to an oil. Chromatography on silica afforded 8 g (17 mmole) of O,O-dibenzyol tartaric di(N-methyl-2-hydroxyethyl)amide (this product elutes with 6% MeOH/CH₂Cl₂).

To the amide product (8.6 mmole) in 50 ml CH₂Cl₂ containing DMAP (0.11 g) and TEA (2.4 ml) was added dropwise, DMT-Cl (8.6 mmole) dissolved in 50 ml CH₂Cl₂. After addition of DMT-Cl the reaction mixture was stirred for 1 hr at 20° C., then the solvent was removed by evaporation. The residue was dissolved in 600 ml ethyl acetate and the organic phase washed with 400 ml 5% NaHCO and 400 ml 80% saturated aqueous NaCl. The organic phase was dried over solid Na₂SO₄. After 30 min the Na₂SO₄ was filtered off, and the supernatant was concentrated to an oil, then coevaporated with toluene and CH₃CN. The crude material was subjected to silica gel chromatography using n-butanol/CH₂Cl₂ for elution. The pure mono-DMT product eluted with 2-3% n-butanol/CH to give 1.53 g (2 mmole) of O,O-dibenzoyl tartaric 2-(O-dimethoxytrityl)hydroxyethyl-N,N-dimethyl, N-methyl-2-hydroxyethyldiamide.

This material was dissolved in 20 ml $CH_2Cl_2$ containing DIPEA (3 mmole). After cooling to 10° C., 2.2 mmole methoxy-N,N-diisopropylaminochlorophosphine was added under argon. After 15 min, ethyl acetate was added, and the organic phase washed with 80% saturated aqueous NaCl, dried over solid $Na_2SO_4$ and evaporated to dryness. After coevaporation with toluene and dry $CH_3CN$, the phosphoramidite residue was dissolved in 10 ml dry $CH_3CN$. This solution was aliquoted into 19 dry Weaton vials and the solvent removed in vacuo. The vials were closed with septum screw caps and stored at $-20°$ C.

This phosphoramidite may be coupled to oligonucleotides using standard DNA synthesis techniques and equipment. After deprotection the resulting linker-containing DNA may be cleaved at the 1,2-diol site as described above.

B.4. Synthesis of a Four-Site Bifurcated Amplification Multimer

For synthesis of branched fragments, a 2000 A control pore glass (CPG) support (30 mg of 7.3 μmole of nucleoside/g) was used. The CPG support was synthesized as described in the commonly owned copending U.S. application Ser. No. 087,158, filed Aug. 18, 1987. An automated methyl phosphoramidite coupling procedure was employed for DNA synthesis as above, except that during the addition of the branched oligonucleotide segments 2.5% (v/v) DCA in toluene (instead of $CH_2Cl_2$) was used for detritylation.

Fragment LLA-2 (GACACGGGTCCTATGCCT; see above) was synthesized on the CPG, then removed from the automated synthesizer and placed into a sintered glass funnel. Manual phosphoramidite couplings were then performed as described (Urdea, M.S., *Methods in Enzymol* (1987) 146:22–41). A 100 μmole aliquot of the $DMT_2$-glycerol phosphoramidite (2-cyanoethyl form) and 250 μmoles of tetrazole were added to the 5'-deprotected fragment and incubated for 15 min. This process was then repeated. Two T methyl phosphoramidites were then added manually and an additional glycerol phosphate was added. The CPG was then placed back on the automated synthesizer and the fragment GATGTGGTTGTCGTACTTTT was synthesized off of each branch. The standard deprotection and purification as above was then employed.

B.5. Synthesis of a Four-Site Comb Amplification Multimer

Using the methods described above, the fragment TTOTTOTTOTTGACACGGGTCCTATGCCT ($O=5'$-DMT-$N^4$-[LevO($CH_2$)$_6$]-5-Me cytidine methyl phosphoramidite) was synthesized. The fragment was then removed from the machine and treated for 1 hr at room temperature with 0.5 M hydrazine monohydrate in 8:2 (v/v) pyridine/concentrated acetic acid. The CPG was then washed with pyridine, then 1:1:2 (v/v/v) $H_2O$/lutidine/THF. The support was then placed back on the automated synthesizer and the fragment was synthesized off of each O in the above formula. The standard deprotection and purification as above was then employed. Note that one copy of the labeled probe (LLA-2) binding fragment is at the 5'-end of the multimer and three copies of the fragment are at the O residues.

Figure 4:
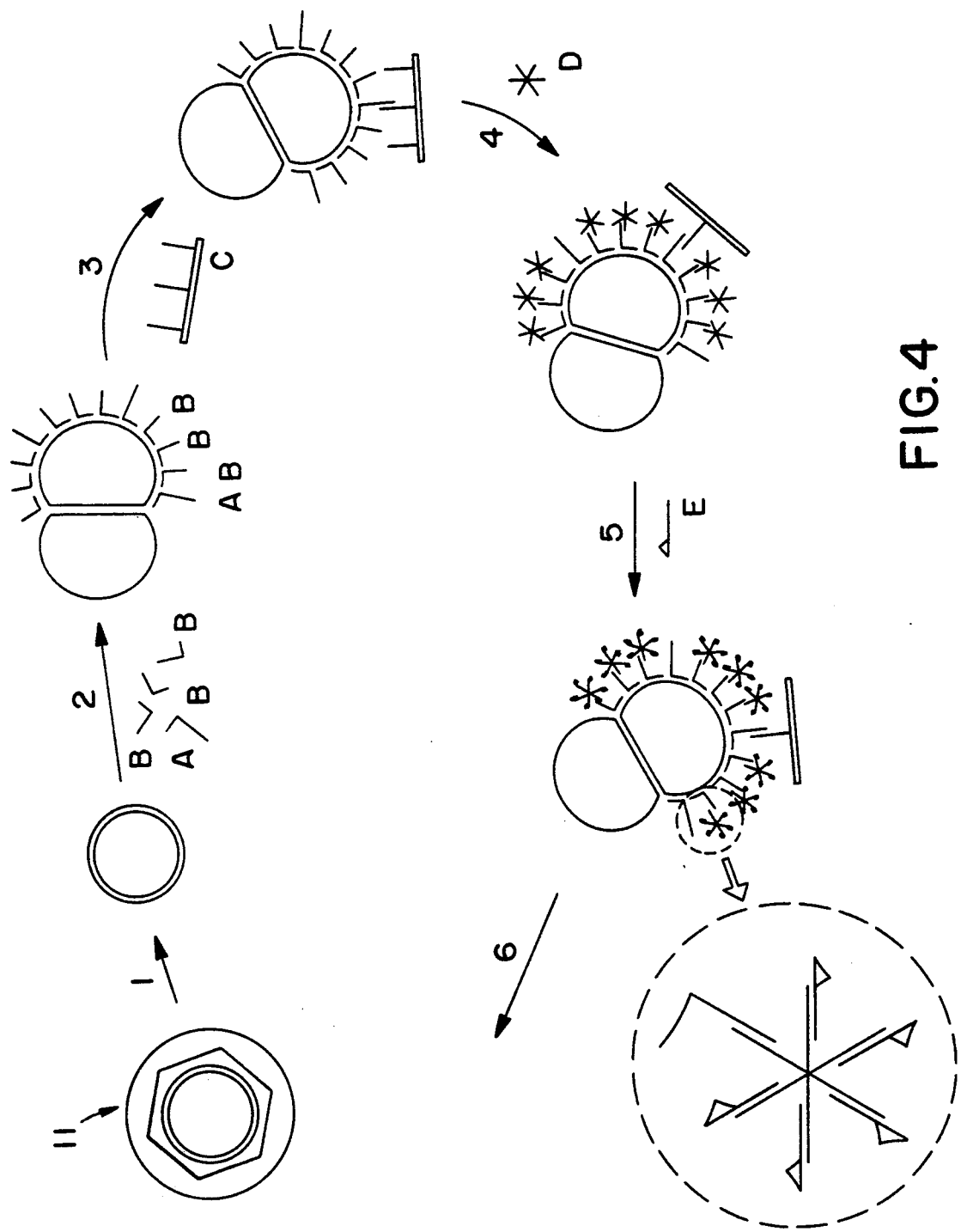
FIG. 4 is a schematic representation of the sandwich hybridization assay described in Example 3.

3. Sandwich Hybridization Assay for Hepatitis B Virus (HBV) DNA Using Multimer FIG. 4 schematically depicts the assay procedure.

A. Standard Analyte HBV DNA

The plasmid pHE63 composed of the entire 3.2 kb HBV genome cloned into the EcoRI site of plasmid pBR[325] linearized with EcoRI and diluted into normal human serum was used as standard analyte. The analyte is designated 11 in FIG. 4.

B. Solid Phase Oligonucleotide Complex (C in FIG. 4)

A 21 base oligomer, 5'-XCACCACTTTCT-CCAAAGAAG-3', where X is as defined above, was synthesized as described in Example 1 and biotinylated using N-hydroxysuccinimdyl biotin in 0.1 M sodium phosphate, pH 7.5. A 5 μl aliquot of this biotinylated fragment (800 pmoles) was added to a 1.5 ml Eppendorf tube containing 500 μl of 0.25% (w/v) 2.8 micron avidin polystyrene beads in 1×PBS. After a 1 h incubation at 37° C., the beads were washed 3 times with 500 μl of 0.1% SDS, 4×SSC by centrifugation then resuspended and stored in the same solution until used.

C. Labeled Oligomer (E in FIG. 4)

An 18 base oligomer, 5'-XGGTCCTAGCCT-GACAGC-3', where X is defined as above, was synthesized, modified with DITC in 95:5 (v/v) dimethylformamide:0.1 M sodium borate, pH 9.3, extracted with n-butanol, and combined with horseradish peroxidase (HRP).

D. Capture Probes (A in FIG. 4)

A set of 12 single-stranded oligomers each having a varying 30 base long portion complementary to a specific sequence of the HBV genome and a constant 20 base long 3'-portion complementary to the oligonucleotide bound to the solid phase was synthesized by the procedures described in Example 1.

E. Amplifier Probes (B in FIG. 4)

A set of 36 single-stranded oligomers each consisting of a varying 30 base long portion complementary to a specific sequence of the HBV genome and a constant 20 base long 3'-portion complementary to the multimer (D in FIG. 4) were synthesized by the procedures described in Example 1.

Both the capture and amplifier probes were designed for the constant ds region of the HBV virus.

F. Bead Assay Procedure 10 l samples of analyte were placed in 1.5 ml Eppendorf tubes and treated with 12.5 μl of proteinase K/SDS (Gene (1987) 61:254) at 37° C. for 30 min. To each sample, 5 μl of 1 M NaOH containing 50 fmoles each of the 48 HBV oligonucleotide probes (12 capture probes and 36 amplifier-probes) were added and the tubes were heated to 100° C. for 10 min. The samples were set on ice for 5 min, microfuged for 10 sec and neutralized with 0.38 M acetic acid, 12.3×SSC (final 4×SSC). Annealing of the probes to the analyte was conducted at 55° C. for 1 h. Subsequently, 25 μl of the capture beads were added and the solution was left at 55° C. for an additional 15 min. Two washes were performed by adding 500 μl of wash solution (0.1% SDS, 4×SSC), vortexing, centrifuging for 1 min and decanting. To each tube, 20 μl containing 50 fmoles of multimer (D in FIG. 4) in HM buffer (0.1% SDS, 4×SSC, 1 mg/ml sonicated salmon sperm DNA, 1 mg/ml poly-A, 10 mg/ml BSA) was added. After vortexing, the tubes were left at 55° C. for 15 min and washed twice as above. Labeling was conducted with 20 µl containing 250 fmoles of probe Type E in HM for 1 h at 37° C. After three washes as above, the beads were thoroughly drained by inversion onto Kimwipes, treated with the appropriate substrate and measured as described below. The total time required for the analysis from addition of the proteinase K/SDS solution to readout was 3 h 50 min in the chemiluminescent format.

The enhanced chemiluminescence method for HRP detection reported by Matthews et al., *Anal Biochem* (1985) 151:205–209, was employed. Beads were taken up in 15 µl of chemiluminescent substrate solution (luminol with p-hydroxycinnamic acid) and then transferred to 8×50 mm Evergreen polypropylene tubes containing 5 µl of 4 mM $H_2O_2$. After 30 sec, tubes were read on a Turner TD-20e luminometer (delay, 10 sec; integration, 20 sec; smoothing, 20 sec). Output was given as the full integral of the light produced during the reaction.

To each tube, a 100 µl aliquot of a fresh o-phenylenediamine solution (OPD; in tablet form from Sigma Chemicals; 50 mg dissolved in 5 ml of 50 mM sodium citrate, pH 5.1, containing 3 µl of 30% $H_2O_2$) was added. After 20 min at 37° C., 50 µl of 4 N $H_2SO_4$ was added to quench the reaction. The beads were then pelleted by centrifugation and the supernatant was transferred to a microtiter dish well. The dish was then read on a Biotek EL310 plate reader set at 490 nm. Longer incubations did not improve the signal to noise ratios.

G. Microtiter Dish Assay Procedure

A microtiter dish assay procedure was employed. Microtiter dishes were prepared as follows. Two types of microtiter dish wells were prepared: (1) N wells for sample work-up and negative controls, and (2) S wells for capture of the probe-analyte complex from samples and positive controls. U N wells were produced as follows: 300 µl of HM buffer was added to Immulon II Remov-a-wells (Dynatech Inc.). The well strips were covered and left standing at room temperature for 1 hour. The HM buffer was removed by aspiration and the wells were washed 3 times with 400 µl of 1×PBS. The strips were covered with plastic wrap and stored at 4° C. until used. Alternatively, wells were coated with poly-phenylalanyl-lysine then with HM buffer, as below.

S wells were prepared from the Immulon II strips as follows. To each well, 200 µl of a 200 µg/ml solution of poly-phenylalanyl-lysine (Sigma Chemical Inc.) in water. The covered strips were left at room temperature for 30 min to 2 hr, then washed as above. A 10 $OD_{260}$ sample of the oligonucleotide of 3B above in 60 µl of 1× PBS was treated with 140 µl of DMF containing 10 mg of ethylene glycolbis(succinimidylsuccinate) (Pierce Chemicals Inc.). The mixture was vortexed and incubated in the dark at room temperature. After 15 min, the solution was passed over a Sephadex G-25 column (PD-10 from Pharmacia), previously equilibrated with 30 ml of 1×PBS. The void volume of the column was diluted to a final volume of 35 ml with 1×PBS. To each well, a 50 µl aliquot of the capture probe solution was added. After covering with plastic wrap, the wells were incubated at room temperature in the dark for 30 min to overnight. The wells were washed with 1×PBS, then coated with H buffer, washed, and stored as above.

Label oligonucleotides were derivatized with alkaline phosphatase (AP) as follows. Calf intestinal AP (3 mg in buffer; immunoassay grade, Boehringer-Mannheim) was placed in a Centricon 30 Microconcentrator. Approximately 2 ml of 0.1 M sodium borate, pH 9.5, was then added and the device was spun at 3500 rpm until a final volume of 40 µl was obtained. The alkylamino oligonucleotide (Section 3C) was then activated with DITC, extracted with butanol, and combined with the protein as described for the HRP probe. PAGE, elution (with 0.1 M Tris, pH 7.5, 0.1 M NaCl, 10 mM $MgCl_2$, 0.1 mM $ZnCl_2$), and concentration as described for the HRP conjugates were employed. The final product was stored at 4° C.

For duplicate analyses, 20 µl of each sample was placed into 2 N wells, then treated with 25 µl of proteinase K/SDS solution. The wells were covered with a Linbro-Titertek microtiter plate sealer, gently agitated, and incubated at 65° C. for 30 min in a water bath. The capture and amplifier probe sets in 1 M NaOH were added in 10 µl to each well. After sealing, the samples were incubated for 10–30 min at 65° C. to 72° C. as above. The solutions were neutralized with 26 µl 0.38 M acetic acid (or 0.76 M 3-[N-Morpholino]propane sulfonic acid (MOPS), free acid), 12.3×SSC, then incubated for an additional 15–30 min covered at 65° C. From each N well, 40 µl of sample was transferred to a new S well containing the solid supported capture probe. The wells were sealed and set at 65° C. for 1–2 hours. Each well was then washed 2 times by aspiration with 0.1% SDS, 0.1×SSC. A solution of amplification multimer (for *N. gonorrhoeae*, penicillin-resistant gonorrhoe and Chlamydia tests; a five-site comb structure (section 2.B.5) was employed) in HM buffer was then added and the samples set sealed in a 55° C. water bath for 15 min to 1 hour. After washing as above, 20 µl of the enzyme-labeled probe in HM buffer was added. Incubation for the HRP probe was carried out for 15 min at 42° C., while the alkaline phosphatase probe was used at 55° C. for 15 min. After washing as above, the appropriate detection reagents were added.

For HRP, the enhanced luminol reagent (see 3F) was used as above.

For AP detection, an enzyme-triggered dioxetane (Schaap et al., *Tet Lett* (1987) 28:1159–1162 and EPA Publication No. 0254051), obtained from Lumigen Inc., was employed. The detection procedure was as follows. For the labeling step 20 µl MM buffer with the AP probe was added to each well and the wells were incubated at 55° C. for 15 min. The supernatant was removed and the wells were washed 2× with 380 µl of 0.1×SSC-0.1% SDS. The wells were then washed 2× with 380µl of 0.1×SSC to remove any remaining SDS. 20 µl of 3.3 ×$10^{-4}$ M dioxetane in CTAB buffer was added to each well. The wells were tapped lightly so that the reagent would fall to the bottom and gently swirled to distribute the reagent evenly over the bottom. The wells were covered with the microtiter plate sealer and incubated in a 37° C. oven for one hour. The wells are then read with a luminometer.

Results

A. Tests on Standard Analyte

The above described assay was carried out on samples containing known amounts of the standard analyte HBV DNA using the multimers of Examples 1–2A. For comparison purposes a three piece assay (bound analyte; oligonucleotide complementary to both analyte and labeled probe; and HRP-labeled probe) was carried out. The comparison assay was assigned a gain value of 1. Gain is the ratio of signal obtained in an amplified assay to signal obtained in an unamplified three piece assay.

The results of these assays are reported in the table below. S/N=signal-to-background ratio.

TABLE 1

| AMPLI-FIER | ASSAY TYPE | GAIN | SIGNAL | BACK-GROUND | S/N |
|---|---|---|---|---|---|
| Enzymatically Ligated Multimer (Ex. 1) | HBV Serum Assay | 29 | 56.2 ± 24.4 @ 10 amole | 12.9 ± 4.73 | 4.4 |
| Chemically Crosslinked Linear Multimer (Ex. 2) | HBV Serum Assay | 25 | 617 ± 116 @ 50 amole | 432 ± 53 | 1.4 |
| Chemically Crosslinked Branched Multimer (Ex. 2) | HBV Serum Assay | 102 | 168 ± 31 @ 10 amole | 17 ± 2 | 9.9 |
| HRP Probe Without Amplifer | 3 Piece Assay | 1 | 32.9 ± 5.7 @ 100 amole | 18.2 ± 1.5 | 1.8 |

B. Tests on Authentic HBV DNA Samples

Authentic HBV DNA samples were identified as follows.

Figure 5:
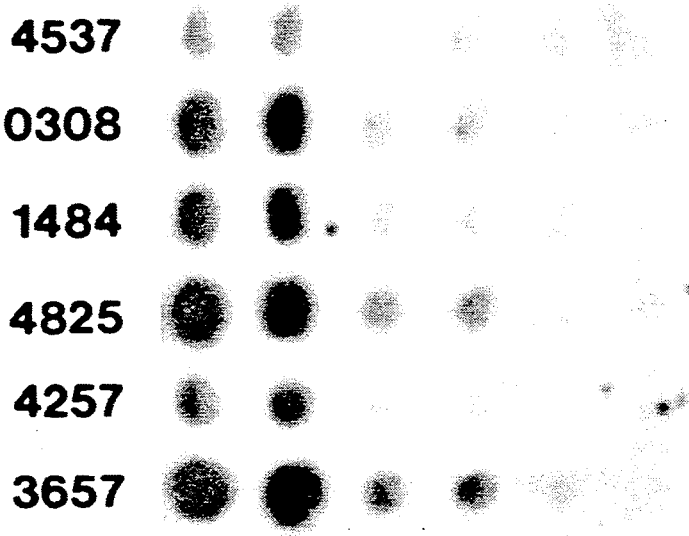
FIG. 5 is an autoradiogram showing the results of the dot blot screening tests described in the examples.

A dot blot screening was conducted for the presence of HBV DNA in 49 HBV surface antigen positive samples using the protein-DNA complex extraction technique of Zyzik et al., *Eur J Chem Microbiol* (1986) 5:330–335. FIG. 5 presents the analysis of the six DNA positive sera found in the set of 49 using $^{32}P$ nick translated pHE63 as a probe. Each sample was blotted and probed in duplicate directly ($10^0$), diluted 1:10 ($10^1$) and 1:100 ($10^2$) in pooled normal human sera. Samples of pHE63 were blotted in duplicate in pooled normal sera or in buffer (10×SSC). Five separate blotting experiments of these sera with dilutions and plasmid standards were performed to establish the ranges calculated. These samples were used in the evaluation of the sandwich hybridization assay of the invention.

Figure 6:
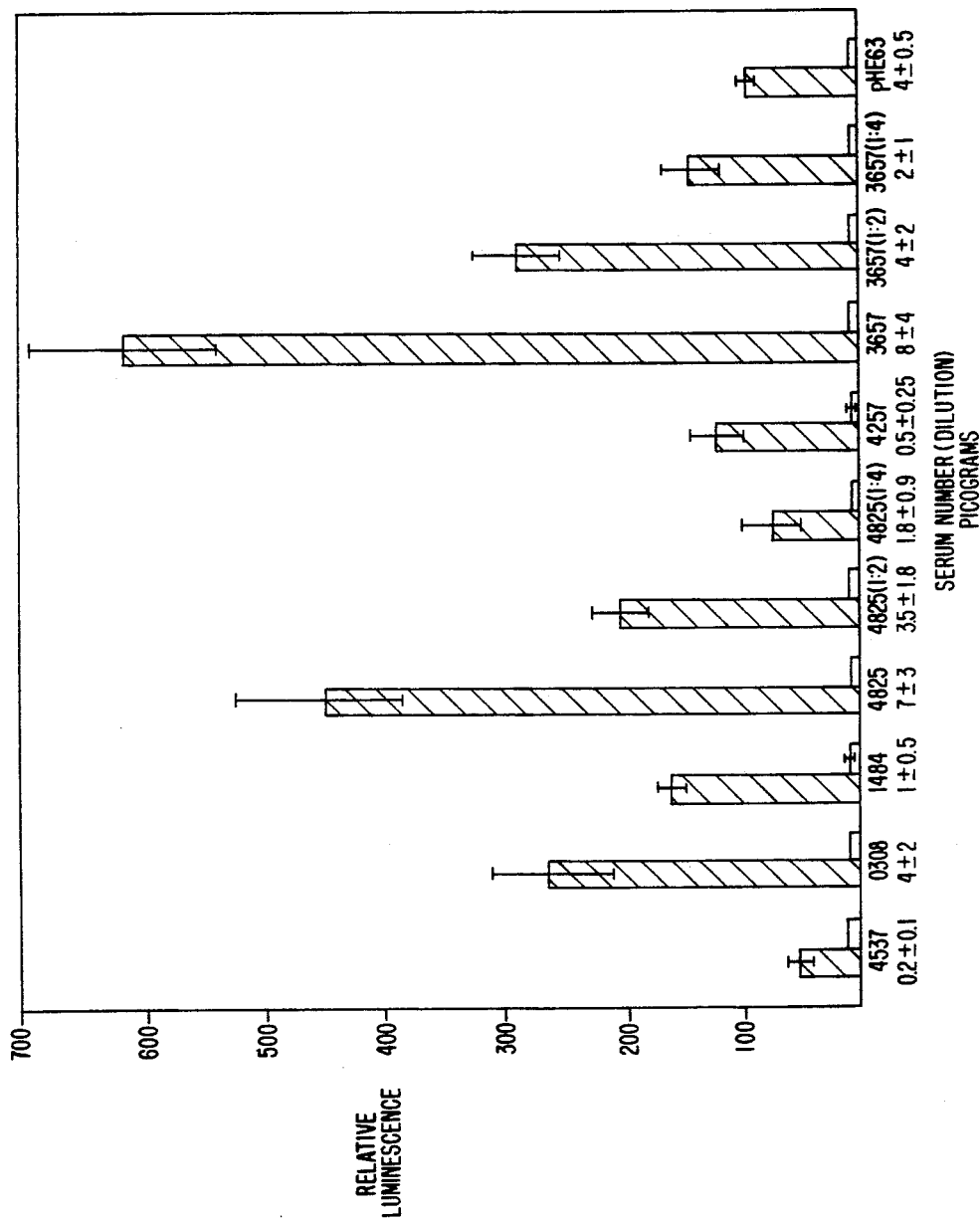
FIGS. 6-8 are bar graphs depicting the results of the tests on authentic HBV DNA samples that are described in Example 4.

FIG. 6 presents the results obtained for the chemiluminescent readout format of the bead capture assay method with the HBV DNA positive samples described above. Analysis of a 4 pg sample of pHE63 is also shown. Two shaded values are given for each sample. The shaded bar represents the absolute signal (S) obtained for each sample and is expressed as the mean for two sets of triplicate samples (6 total samples). The open bar indicates the same number of control samples run on the same sera using beads that do not contain the Type C capture probe. This control, which is not possible in a blotting assay format, was used to determine nonspecific binding or noise (N) for each sample matrix that might lead to false positive signals. The specific signal for each sample can be expressed as the ratio of S and N as defined. An S/N ratio of 1 indicated no specific binding. Minimal S/N ratios indicating a positive sample are discussed below.

S/N ratios ranged from 3.9 to 49 for sera containing between 0.2 and 8 pg of HBV DNA. Assays conducted on two and four fold dilutions of sera 4825 and 3657 into pooled normal human sera resulted in a near linear decrease in the absolute signals for each sample, substantiating the presumed specific nature of the method. Excellent run to run reproducibility was found for all samples with different lots of beads and reagents. Although samples were read only 30 sec after addition of the chemiluminescent substrate solution, equivalent results were obtained for up to 45 min. Also, longer signal integrations did not improve S/N ratios. The sera employed ranged from cloudy to clear in appearance, were stored frozen and freeze-thawed many times. No attempt was made to clarify the samples prior to hybridization analysis. Increased solution hybridization or bead capture times (up to 18 h) did not significantly increase the S/N ratios.

Figure 7:
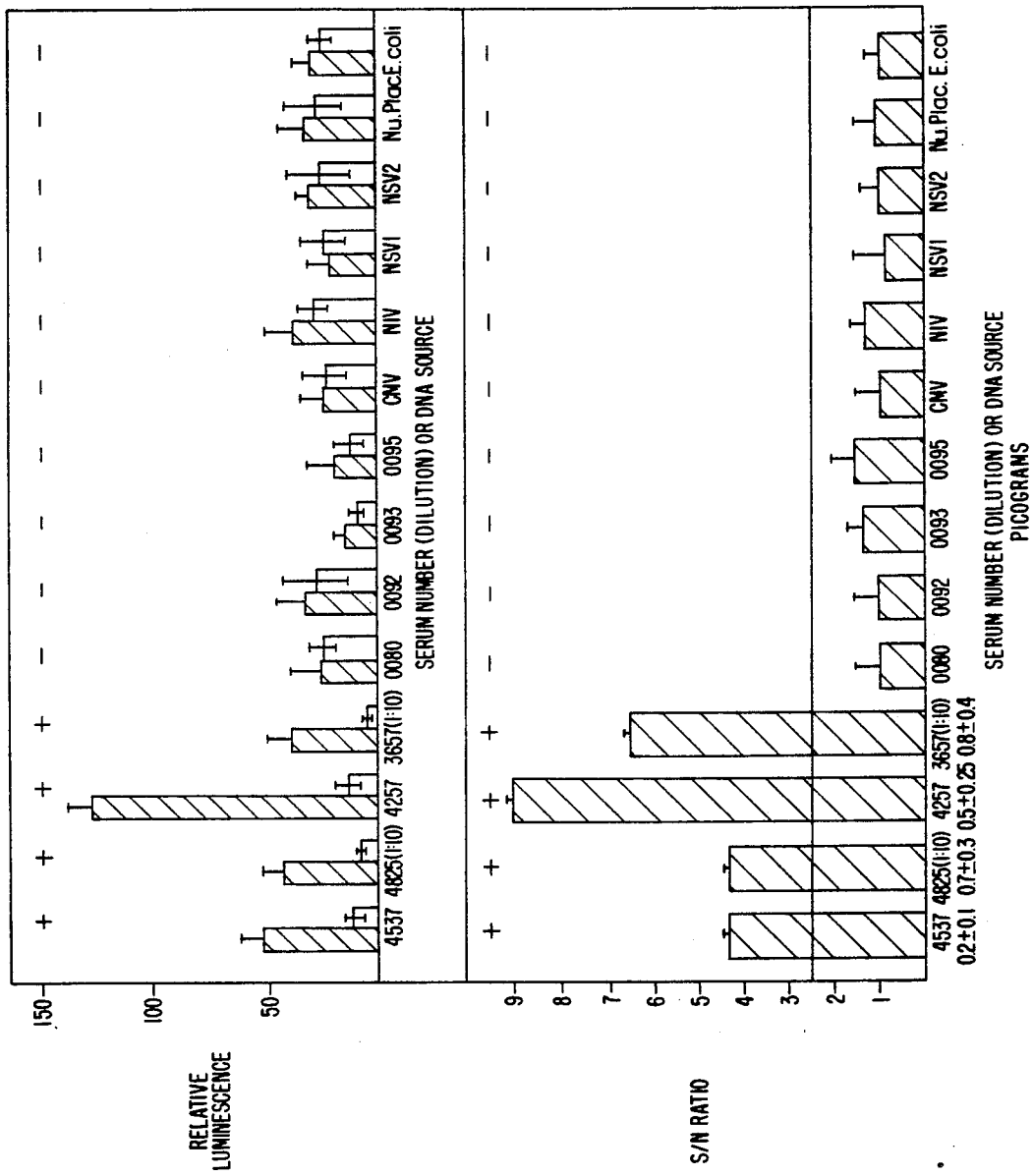

In FIG. 7 the analysis of subpicogram HBV DNA samples are compared to known negative sera and large quantities of heterologous nucleic acids in pooled sera. Although the S value for the lowest positive serum employed (upper panel; 1 to 10 dilution of serum 3657) is slightly higher than the highest S for a negative serum (0092) or non-HBV DNA (HIV), no clear cutoff to differentiate between true and false positives below the pg level was possible based on absolute S alone. However, if the S/N was compared for these same samples (lower panel), a cutoff of S/N=2.5 permitted a clear distinction to be made. No negative sample had a value higher than 1.7, yet the lowest positive at 0.2 pg had an S/N=4.3. This clearly demonstrates the value of using a nonspecific binding control for each sample.

Figure 8:
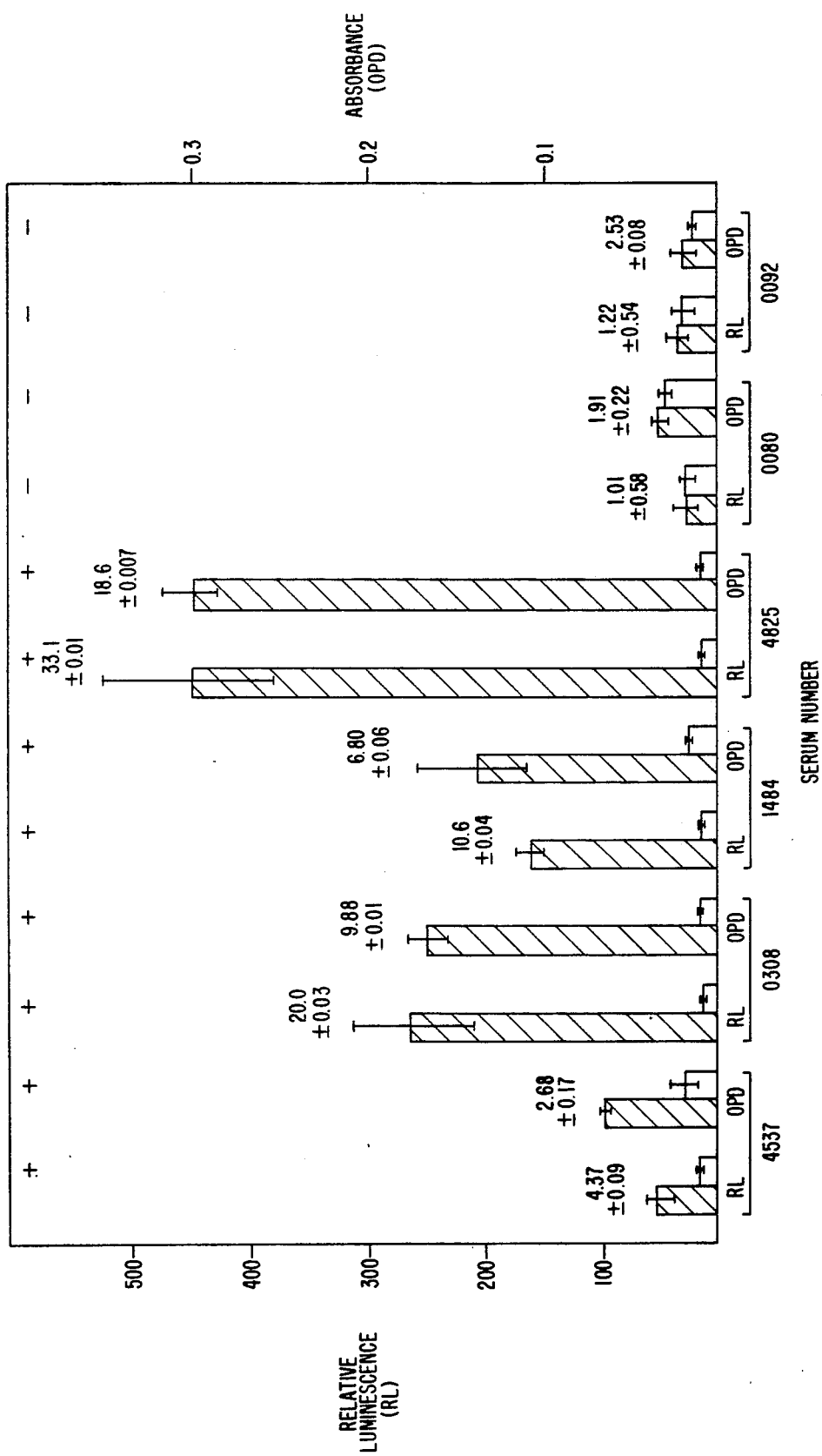

In FIG. 8, a comparison is made between an assay conducted on HBV DNA positive and negative sera using both the luminol-p-hydroxycinnamic acid (given as relative luminescence, RL) and o-phenylenediamine (OPD) detection. Although the methods were comparable in sensitivity, the chemiluminescent method was preferred for several reasons. Firstly, using the bead format, the best colorimetric results were obtained by conducting the OPD reactions in Eppendorf tubes and transferring the solution to a microtiter dish for reading on an ELISA reader since the scattering from beads proved to be a significant source of background. In contrast, beads did not interfere with the chemiluminescent readout on the luminometer. Secondly, the chemiluminescent method was considerably faster. As opposed to waiting 30 min after addition of OPD before the detection, the chemiluminescent reactions could be read rapidly 30 sec after addition of the substrate. Lastly, there was a 1.5- to 2-fold increase in the S/N using RL versus OPD.

4. Sandwich Hybridization of *N. gonorrhoeae* DNA

Based on the *N. gonorrhoeae* pilin sequence described by Bergstrom, S., et al., *Proc Natl Acad Sci USA* (1986) 83:3890–3894, twelve amplifier DNA probes and three capture DNA probes were synthesized by the automated phosphoramidite method as described by Warner et al., supra. Purification was carried out according to Sanchez-Pescador and Urdea, supra. The 5'-portions of the probes were complementary to segments of the pilin sequence and were as follows:

| Probe Designation | 5'-Sequence |
|---|---|
| Amplifier | |
| GCP-LLA2C-1 | ATACTTATGGGAAGTTTTTCCGAAATGGGA |
| GCP-LLA2C-2 | GCTCGACTACTAACACTAGCGATAGCAGCC |
| GCP-LLA2C-3 | AAACCGCAATCAGCGGGAAGGGCGGATGGT |
| GCP-LLA2C-5 | GGAAAACCGGCTTCCAGTTTTTAGTCGGCA |
| GCP-LLA2C-6 | GCTCATAATGGACTTAAGGCCGTTTACCGG |
| GCP-LLA2C-7 | TTTGTTGTGAAGACGGCCGCACCGTAGGGG |
| GCP-LLA2C-9 | ACTTCAATTTTTGCCGCAGCAATGGCGGTG |
| GCP-LLA2C-10 | CGAAAGTTCGCCGCATTTGTTACTAATGTT |
| GCP-LLA2C-11 | GTTTTTTGAGAGGGACACCCGGTCCGCACT |
| GCP-LLA2C-13 | ATGCGCGTGGCTGCTGCTGTGGCAACGGCT |
| GCP-LLA2C-14 | GTTTCTGCCGTTTCTTTAGCTGTGGTTCGT |
| GCP-LLA2C-15 | CGGCAGTTGGACGGCGCTATTCCGTAGACT |
| Capture | |
| GCP-XT1-4 | GATGTGGCGGGCGCGCGTTCAAAGGCTTCG |
| GCP-XT1-8 | GAGGCTGTAGTTTCCGTTTATACAATTTCT |
| GCP-XT1-12 | GCCAAGCCATTTTACCAAGACGCCTGTCGG |

The 3'-portion of each amplifier probe was constructed to be complementary to the linear multimer of 2A above.

The 3'-portion of each capture probe was constructed to be complementary to the sequence of the oligonucleotide of the solid phase oligonucleotide complex of 3.B above.

Analyte DNA isolated from an *N. gonorrhoeae* strain, an *N. meningitiditis* strain, and several nonpathogenic commensal strains of Neisseria were tested using the *N. gonorrhoeae* amplifier and capture probes according to the assay format described in 3.G above. The results of these tests are reported in the table below.

| Assay Signal Response of Neisseria Species | |
|---|---|
| Sample | S/N[a] |
| Positive[b] species: | |
| *N. gonorrhoeae* | |
| (1) Clinical isolates[c] | 6.8–187.0 |
| (2) Geographical distribution[d] | 48.6–239.5 |
| *N. meningitiditis* | |
| (1) Serogroup A (#9205) | 5.8 |
| (2) Serogroup B (#9206) | 15.4 |
| (3) Serogroup C (#9207) | 12.9 |
| (4) Serogroup 29E (#9218) | 18.1 |
| (5) Serogroup X (#9210) | 31.2 |
| (6) Serogroup Z (#9211) | 15.5 |
| Negative[b] species: | |
| *N. meningitiditis* | |
| (1) Serogroup E (#9209) | 2.1 |
| (2) Serogroup W135 (#9212) | 1.9 |
| *N. cererea* | |
| (1) #36263 | 0.92 |
| (2) #33683 | 0.76 |
| (3) #32824 | 0.83 |
| (4) #32828 | 0.99 |
| (5) #30003 | 2.1 |
| *N. lactamica* | |
| (1) #30011 | 0.92 |
| (2) #36016 | 1.1 |
| (3) #37168 | 1.7 |
| (4) #37170 | 0.72 |
| (5) #37174 | 0.97 |

[a]Signal obtained with 6 × 10[6] to 2 × 10[8] cells. Noise was defined as the relative luminescence obtained for buffer alone.
[b]A sample with a S/N > 3 was defined as positive; and a sample with a S/N < 3 was defined as negative.
[c]Urethral swab samples, 46 male and 56 female, were obtained from Highland Hospital, Oakland, California.
[d]Samples were obtained from Boston, Denver, New York, Indianapolis, Peoria, Portland, San Diego, San Francisco, Kentucky, Minnesota and North Carolina.

5. Sandwich Hybridization for *N. gonorrhoeae* Using Branched Amplification Probe This example exemplifies the use of abandoned amplifier probe or two multimers in hybridization assays: one that binds to the analyte; and a second that binds to the first and provides sites for binding labeled oligomers.

Twelve 5'-phosphorylated 40-base *N. gonorrhoeae* pilin specific probes were synthesized and purified. The sequences of these probes (probes 1, 2, 3, 5, 6, 7, 9, 10, 11, 13, 14 and 15) are shown below and were designed to contain 30 unique bases complementary to the pilin gene (3'-end) and 10 common bases (5, end; pAGTACGTTTA).

Probe-1 pAGTACGTTTAAGG-GTAAAGCCTTTTTGAAGGGTATTCATA

Probe-2 pAGTACGTTTACCGACGATAGCGAT-CACAATCATCAGCTCG

Probe-3 pAGTACGTTTATGGTAGGCG-GGAAGGGCGACTAACGCCAAA

Probe-5 pAGTACGTTTAACGGCTGATTTTT-GACCTTCGGCCAAAAGG

Probe-6 pAGTACGTTTAGGCCATTTGCC-GGAATTCAGGTAATACTCG

Probe-7 pAGTACGTTTAGGGGATG-CCACGCCGGCAGAAGTGTTGTTT

Probe-9 pAGTACGTTTAGTGGCGGTAAC-GACGCCGTTTTTAACTTCA

Probe-10 pAGTACGTTTATTGAATTCATTGTT-TACGCCGCTTGAAAGC

Probe-11 pAGTACGTTTATCACGCCTGGC-CCACAGGGAGAGTTTTTTG

Probe-14 pAGTACGTTTATGCTTGGTGT-CGATTTCTTTGCCGTCTTTG

Probe-15 pAGTACGTTTATCAGATGCCT-TATCGCGGCAGGTTGACGGC

The common bases were used to incorporate by enzymatic ligation a common fork-type branched extension (5'-AGGCATAGGACCCGTGTCTTYTTYT-TATCGTTATTC-3'; Y = 5-methyl-N[4](6-hydroxyhexyl)deoxycytidine incorporated as the 5'-hydroxyl, N[4]-hydroxyhexyl bis-dimethoxytrityl derivative; FTE-1) with a complementary linker, 5'-TAAACGTACT-GAATAACGAT-3', (LINK-1). The capture probe set (probes 4, 8 and 12) were those described for the assay of 4 above.

The branched amplifier probes are synthesized by ligation and purification in batch 650 pmoles each of probes 1, 2, 3, 5, 6, 7, 9, 10, 11, 13, 14 and 15, 7 nmoles of LINK-1, and 5.7 pmoles of FTE-1 as generally described in Meth Enzymol (1987) 146:22-41 to yield 934 pmoles of product.

An alkaline phosphatase labeled probe complementary to the 5'-secondary sequences of the branched amplifier probes was prepared according to section 3.G above.

Assays for N. gonorrhoeae were conducted using a pilin gene containing plasmid as described above. A total of 4-5 fmoles of each capture and amplifier probe was employed. A total of 200 fmoles of the multimer and the alkaline phosphatase-labeled probe were used. The procedure was identical to 4 except that no amplification step was used. For comparison purposes assays using the probe set of 4. above were run side-by-side. The results are shown below.

|  | Signal | Noise | S/N |
|---|---|---|---|
| Comparison (4 above) | 5.4 ± 0.3 | 0.2 ± 0.02 | 22.8 ± 2.0 |
| Branched amplifier system | 10.6 ± 1.4 | 0.1 ± 0.0 | 75.8 ± 9.8 |

A branched multimer was synthesized using the techniques described in 2.B above that contained both comb- and fork-type structural components. It was necessary to construct the molecule as described since a 5, maximize binding to the branched labeling probe set (as opposed to the 3, extension described above). The multimer had the following structure

Figure 9:
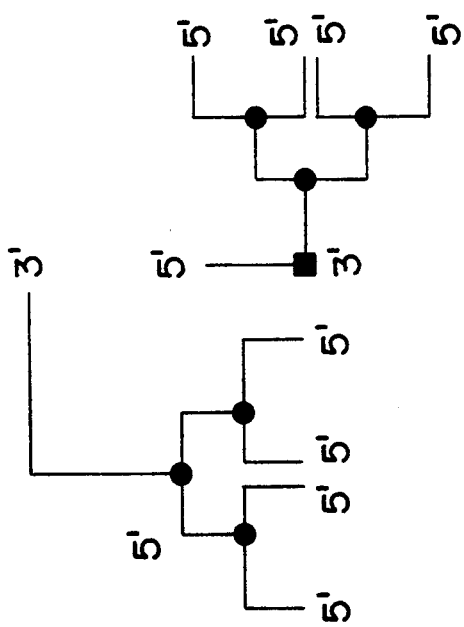
FIG. 9 depicts schematically the multimers used in the assay described in Example 5.

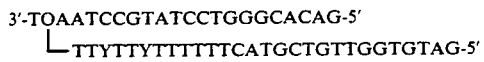

where Y is defined as above and O=5-methyl-$N^4$(6-hydroxyhexyl)deoxycytidine incorporated as the 5'-O-dimethoxytrityl, $N^4$-0-FMOC derivative of 5-methyl-$N^4$(6-hydroxyhexyl)deoxycytidine. The branched amplifier probe and branched multimer described above are depicted schematically in FIG. 9.

Assays for N. gonorrhoeae were conducted as described above with an amplification step. Side-by-side analyses with the probe set of 4 were also performed. The results are given below.

|  | Signal | Noise | S/N |
|---|---|---|---|
| Comparison (4 above) | 5.5 ± 0.8 | 0.3 ± 0.03 | 21.0 ± 3.8 |
| Two multimer system | 17.3 ± 1.7 | 0.4 ± 0.1 | 45.5 ± 12.2 |

6. Sandwich Hybridization Test for TEM-1 beta-Lactamase DNA in N. gonorrhoeae Molecular analyses have revealed that the penicillin resistance observed in N. gonorrhoeae is mostly due to the presence of a TEM-1 beta-Lactamase gene in a non-conjugative plasmid of 3-7 Mdal. (This plasmid is homologous to those found in H. ducreyi, H. parainfluenzae, and occasionally H. influenzae.) Probes were thus developed to detect TEM-1 DNA in N. gonorrhoeae (or the other mentioned bacteria carrying homologous plasmids) for the purpose of determining penicillin resistance.

Figure 10:
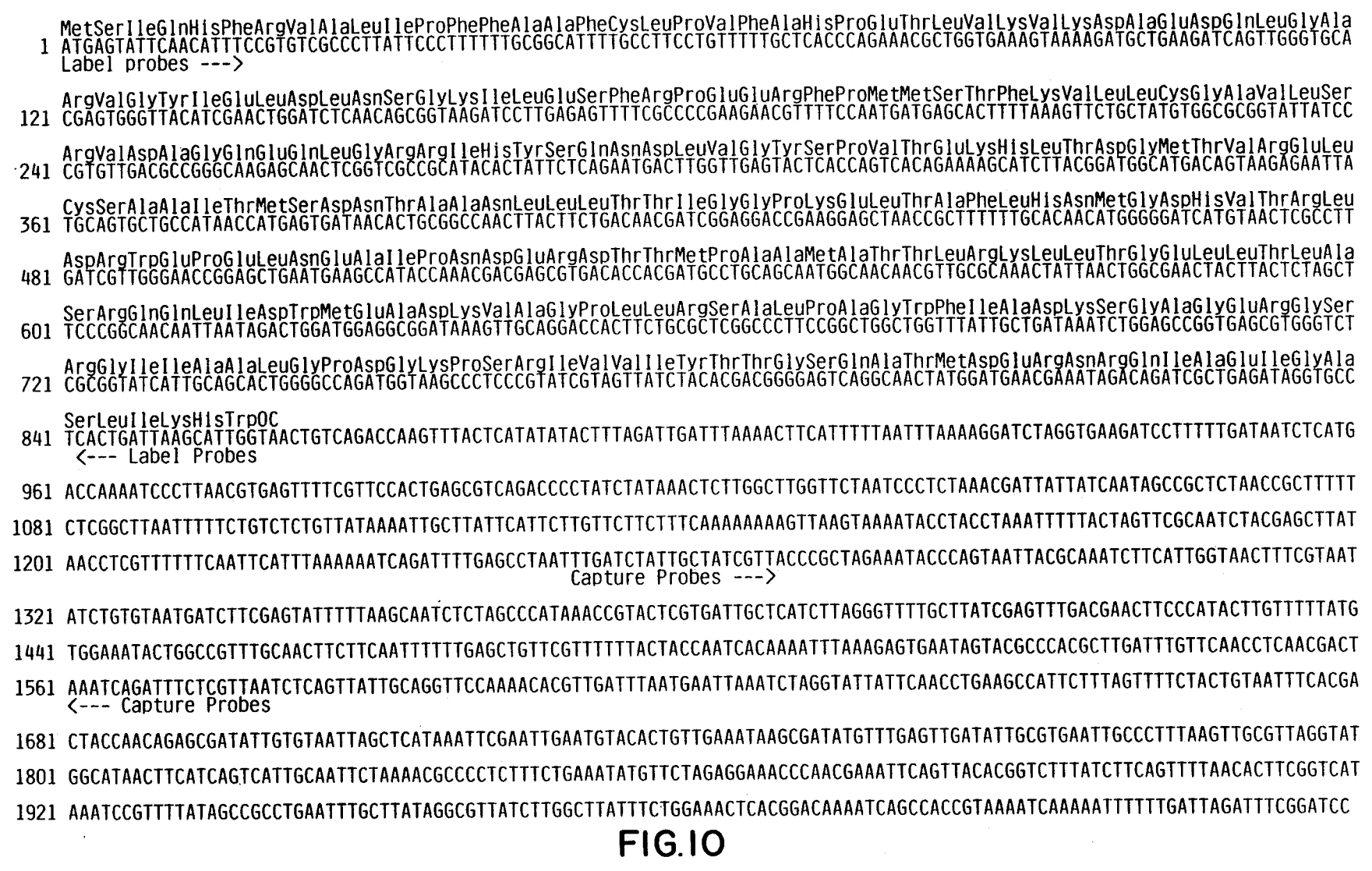

The 7.3 Kb N. gonorrhoeae plasmid carrying the TEM-1 gene was obtained as described by Maniatis, Molecular Cloning: A Laboratory Manual, Cold Spring Harbor Laboratory (1982). This plasmid was transformed into E. coli HB101 and purified. The plasmid was digested with BamHI and a 2390 bp BamHI fragment was purified and partially sequenced. A total of 1811 bp were sequenced, corresponding to 80% of the structural TEM-1 gene and 1181 bp of adjacent sequences from the H. parainfluenzae plasmid related to pHPA300 DNA. The sequenced portion is shown in FIG. 10.

Amplifier probes and capture probes were synthesized and purified by the procedures described above. The 5'-portions of the amplifier probes were complementary to sequences of the coding region; whereas the 5'-portions of the capture probes were complementary to sequences of pHPA300. The sequences of the probes are shown in FIG. 11.

Amplifier and capture probes were also prepared using a similar strategy to that used for the HBV and N. gonorrhoeae probes in which both sets of probes are directed to the TEM-1 gene. The sequences of these probes are shown in FIG. 12.

The assay format of 3.G. above was used to assay crude cellular lysates from different bacteria. The results of these tests are tabulated below with the designations "TEM-1" indicating tests using the probes directed only to the TEM-1 gene and "TEM-1NH" indicating the tests where the probes are directed, respectively, to the TEM-1 gene and pHPA300 sequences.

TABLE 2

| Screening of Penicillin-Resistant Bacteria | | | | |
|---|---|---|---|---|
|  | TEM-1 | | TEM-1NH | |
| Species | Pos. | Neg. | Pos. | Neg. |
| Neisseria gonorrhoeae | 2 | 0 | 97 | 0 |
| Haemophilus parainfluenzae[1] | nd[2] | nd | 3 | 0 |
| Haemophilus influenzae[3] | 2 | 0 | 0 | 2 |
| Haemophilus ducreyi | nd | nd | 3 | 0 |
| Salmonella typhi | 2 | 0 | 0 | 2 |
| Shigella sonnei | 1 | 0 | 0 | 1 |
| Branhamella catarrhalis | 0 | 4 | 0 | 4 |
| Escherichia coli | 1 | 0 | 0 | 1 |

[1]Isolated from respiratory tract.
[2]Not determined.
[3]Isolated from genital tract.

Based on the above tests and additional tests, the specificities of the TEM-1 and TEM-1NH assays may be defined as follows:

Penicillin Resistant Organisms Positive with the TEM-1 Assay: Penicillinase Producing Neisseria gonorrhoeae (PPNG), H. influenzae, H. parainfluenzae, S. typhi, S. sonnei, E. coli.

Penicillin Resistant Organisms Positive with the TEM-1NH Assay: PPNG, H. influenzae, H. parainfluenzae, H. ducreyi.

Penicillin Resistant Organisms Negative with the TEM-1NH Assay: H. influenzae, S. typhi, S. sonnei, E. coli, B. catarrhalis non-TEM-1 β-lactamase.

Penicillin Sensitive Organisms Negative with the TEM-1NH Assay: N. gonorrhoeae, B. catarrhalis, H. ducreyi, N. cinerea, Clostridium albians, N. lactamica, N. mucosa, N. sicca, N. subflava, N. meningitidis, H. influenzae, Streptococcus faecalis, Mycoplasma hominis, Treponema pallidum.

This TEM-1 assay is thus a powerful clinical tool that will enable medical personnel to identify penicillin-resistant infections and prevent treatment failure by choosing the appropriate antibiotic for therapy.

7. Sandwich Hybridization for Chlamydia trachomatis

A. Probes/Multimers

Amplification and capture probes sets were prepared using the same strategy as that used to prepare HBV and TEM-1 probes and were designed to hybridize to the Chlamydia pCHL2 plasmid. (Palmer and Falkow, *Plasmid* (1986) 16:52–62.) Each probe of the set was a 50 mer, with the first 30 nucleotides (5' to 3') being complementary to pCHL2 sequences and the last 20 nucleotides being the amplifier and capture sequences used in the TEM-1 and TEM-1NH assays. The pCHL2 sequences for these probes are given below:

| Probe Designation | Sequence (3' to 5') |
|---|---|
| Amplifier | |
| pCHL2.C LLA2C-2 | CTACTAAACTCGCACACATCGCGACTTCTT |
| pCHL2.C LLA2C-3 | AACTCATTAAAGTAAAAGGCGAGCAAATTA |
| pCHL2.C LLA2C-4 | ATGTTACTTTTAGGTAACGCATCTAGAGGC |
| pCHL2.C LLA2C-6 | TCACGATATCGTTTCTGAAAAAGATAAGCG |
| pCHL2.C LLA2C-7 | CGATCTCCGGCCAGATAAATACTATATAAG |
| pCHL2.C LLA2C-8 | GTCAGTCTTTAACCTCACGACCGAGCATAT |
| pCHL2.C LLA2C-10 | AGAAAGAAACTACGGAAGGGTTGTCCTATG |
| pCHL2.C LLA2C-11 | CTATAACTACTATTTCCTCAATAGAATCGA |
| pCHL2.C LLA2C-12 | CCATTAAAGCACTAATATCGTCGATCCGGT |
| pCHL2.C LLA2C-14 | TATTTAGAACGCCAATGAGTTGTCGCATCT |
| pCHL2.C LLA2C-15 | CCAAAGGATAGAGATCTTTACTCGCGTCCA |
| pCHL2.C LLA2C-16 | TAACAACTCGCCTAATAACGATTAAATTGT |
| pCHL2.C LLA2C-18 | AGATTTCTTCTTAATAAGGCTCATCTTCTT |
| pCHL2.C LLA2C-19 | CCTCTTTGTCAATCTCTTAGTGTAAAAATA |
| Capture | |
| pCHL2.CXTI-1 | TTCGAATCTAGGCAAAGAGTATGCCAAAAG |
| pCHL2.CXTI-5 | GATAACGAACTCGCATATTTCCCTTCCGAA |
| pCHL2.CXTI-9 | TTTTCTGCTCGTTGCAAGAGACTCTTAGTT |
| pCHL2.CXTI-13 | TATCCCTTTTGACGAAATCGATATCTGTAC |
| pCHL2.CXTI-17 | TATAGACCACTTTTTAATGTTTCTCCCCTA |

B. Samples Tested and Results

Assays were performed on isolated elementary bodies (EB) of Serovar L$_2$. The concentration of EB in standard samples was determined by spreading dilutions in 1×PBS onto a slide and staining with the Syva Microtrak Immunofluoresc-ence Kit. By microscopic examination, six random fields were counted and the total EB per ml was calculated.

The sample preparation procedure for *Chlamydia* differed from the HBV or *Neisseria*. One of two methods was employed: 12.5μl of either (1) lysozyme (4 mg/ml in 50 mM glucose, 25 mM Tris, pH 8.0, 10 mM EDTA) or (2) 10 mM DTT in 1×PBS was added to each well containing 10μl of sample. After incubation at 65° C. for 30 min, 1.2 μl of 10% SDS was added. The assay was then conducted as described above. Prior to the capture step, 10 μl of horse serum was added to the N and S wells. Also, for the amplification and labeling steps, horse serum instead of water was used in the HM buffer. The alkaline phosphatase/phosphate dioxetane system was employed for detection, as above. The results were as follows.

| Number of EB | Signal |
|---|---|
| 3 × 10$^6$ | 22.67 ± 1.63 |
| 6 × 10$^5$ | 5.39 ± 0.12 |
| 3 × 10$^5$ | 2.07 ± 0.11 |
| 1.5 × 10$^5$ | 1.63 ± 0.03 |
| 0 | 0.57 ± 0.06 |

8. Sandwich Hybridization Test for tetM Determinant in *N. gonorrhoeae*

*N. gonorrhoeae* strains resistant to high levels of tetracycline resistance exhibiting MIC (minimum inhibitory concentration) values above 16 μg/ml have been found to have acquired the tetM determinant in a 24.5 Md conjugative plasmid (Annual Review of Microbiology (1984) 38:111–133 and Antimicrobe Agents Chemother. (1986) Vol 30:664–670). An assay was thus developed to detect the tetM determinant in *N. gonorrhoeae* to permit direct diagnosis of tetM mediated tetracycline resistance in clinical samples. The assay allows detection of tetM from large numbers of samples, gives "same day" results, and is capable of detecting as few as 15×10$^3$ cells.

Ten μl of tetracycline resistant *N. gonorrhoeae* (TRNG) cells suspended in either GC broth or skimmed milk were mixed with 12.5 μl of lysis solution (2 mg/ml proteinase K in 10 mM Tris-HCl, 150 mM NaCl, 10 mM EDTA, 1% SDS, pH 8.0) in a clear Immulon II well (Dynatech), and incubated at 65° C. for 20 min.

Amplification and capture probes sets were prepared using the same strategy as that used to prepare the HBV and TEM-1 probes and were designed to hybridize to the tetM structural gene. The sequences of the probes were based on the tetM gene sequence from the streptococcal conjugative shuttle transposon Tn1545 described in *Nucleic Acids Research* (1986) 14:7047–7058. The sequence of the tetM gene together with the capture probe (A) and amplifier probe (B) sequences are shown in FIG. 13. Each probe was a 50 mer with the first 30 nucleotides (5' to 3') being complementary to the tetM gene (as shown in FIG. 13) and the last 20 nucleotides (extended at the 3' end) being CTTCTTTGGAGAAAGTGGTG for the capture probes and TTAGGCATAGGACCCGTGTC for the amplifier probes.

The test procedure was similar to the microtiter dish assay procedure of 3.G. above. Five μl of 1 M NaOH containing 0.2 pm of each capture and labeling probes were added and the mixture was incubated at 65° C. for 20 min. Thirteen μl of neutralizing solution (2M MOPS, 12.3×SSC (1×SSC=0.15 M NaCl, 15 mM sodium citrate) were added and the mixture was incubated at 65° C. for 15 min. After ten μl of heat inactivated horse serum was added to each well, the solutions were mixed and transferred to Immulon I white wells previously coated with a synthetic oligonucleotide complementary to the capture probes. The wells were incubated at 65° C. for 2 hours after which the mixture was removed from the wells and discarded. The wells were washed twice with 0.1% SDS, 0.1×SSC. Forty μl of a solution of amplification multimer (see 3.G. above) were added and the wells were incubated at 55° C. for 15 min. The wells were then washed twice as above and 40 μl of an alkaline phosphatase labeled oligonucleotide probe (see 3.G. above) solution were added. The wells were further incubated at 55° C. for 15 min, washed twice as above and washed twice with 0.1×SSC. Detection was achieved with a dioxetane chemiluminescent substrate (see 3.G. above). Luminescence was recorded either by using a microtiter dish reading luminometer (Dynatech) or by exposing the wells at Polaroid 57 instant black and white film in a dark chamber at 37° C. for 10 min. The signal to noise ratio (S/N) is defined as the light counts emitted by a well containing a sample divided by the light counts emitted by a well containing buffer alone. A sample was considered positive when the S/N ratio was ≧3.

For comparison, tetracycline sensitive (Tc$^s$) strains and commensal strains known to carry tetM were also tested. The table below presents the results of the tests.

| strain[1] | tetM positive | tetM negative |
|---|---|---|
| N. gonorrhoeae | 132 | 0 |
| N. gonorrhoeae (Tc$^s$) | 0 | 45 |
| N. mucosa | 4 | 0 |
| N. mucosa/perflava | 1 | 0 |
| N. perflava/sicca | 9 | 0 |
| K. denitrificans | 3 | 0 |
| E. corrodens | 1 | 0 |

[1]-All organisms were resistant to tetracycline (MIC ≧ μg/ml) except where indicated.

As shown in the table, a total of 132 TRNG strains were tested using the tetM hybridization assay. All of these strains showed positive values when read with the luminometer or with instant film. Commensal strains known to carry tetM, such as *N. mucosa*, *N. mucosa/perflava*, *N. perflava/sicca*, *Kingella denitrificans* and *Eikenella corrodens*, were also positive in the assay. On the other hand, none of the 45 Tc$^s$ strains tested showed positive values.

This assay may be used to detect any tetM mediated tetracycline resistant organism. By designing the capture and amplifier probes to bind to both the tetM gene and the 24.5 Md plasmid in an appropriate arrangement (as in the TEM-1NH assay described above), reactivity may be limited to TRNG. The use of the tetM test, together with the TEM-1 test reported above considerably reduces the time required to screen for antibiotic resistant microorganisms where TEM-1 or tetM mediated resistance is suspected. These procedures obviate the need for subculturing primary cultures in the presence of the appropriate antibiotic. These assays require minimal sample preparation and involve very simple manipulations similar to ELISA procedures. In combination with the assay for *N. gonorrhoeae*, detection of *N. gonorrhoeae* and antibiotic resistance characterization can be conducted in a few hours. All the components of the assay, including the microtiter wells, are universal (analyte independent) with the exception of the capture and amplifier probes. As a result, the simultaneous analysis of a sample for the infectious agent and the antibiotic resistance can be performed in parallel, within the same time frame, and with the same manipulations.

9. Sandwich Hybridization Assay for *N. gonorrhoeae* DNA using Probes Based on *N. gonorrhoeae* Genomic Sequence SSJK1

A new genomic sequence designated SSJK1 having a high degree of specificity for *N. gonorrhoeae* was identified by screening genomic clones against *N. gonorrhoeae* DNA and *N. meningitidis* DNA and selecting sequences that reacted with the former but not the latter. The DNA sequence of SSJK1 is shown in FIG. 14. This sequence was checked against available DNA libraries and has not been reported previously.

Based on the SSJK1 sequence, capture and amplifier probes were synthesized as in section 4 above. The 5' portions of the sequences are shown in FIG. 15. The 3' portions of the sequences were the same as those described in the TEM-1 assay described above (see FIG. 12). Both 5' portions and 3, portions are shown in FIG. 15. The assay format of 3.G. above was used to assay crude cellular lysates and genomic DNA from different bacteria. The results of tests with DNA samples are tabulated below.

| Sample | S/N |
|---|---|
| 1) Negative samples$^a$ | |
| a) *Branhamella catarrhallis* | 0.97 |
| b) *Neisseria sicca* | 1.12 |
| c) *Neisseria subflava* | 1.08 |
| d) *Neisseria mucosa* | 1.02 |
| e) *Neisseria lactamica* | 1.94 |
| f) *Neisseria flavescens* | 1.09 |
| g) *Neisseria cinerea* (#33683) | 2.21 |
| h) *Neisseria cinerea* (#32828) | 2.23 |
| i) *Neisseria meningitidis*, serogroup A | 1.94 |
| j) *Neisseria meningitidis*, serogroup B | 1.12 |
| k) *Neisseria meningitidis*, serogroup C | 1.19 |
| l) *Neisseria meningitidis*, serogroup D | 0.92 |
| 2) Positive samples$^b$ | |
| *Neisseria gonorrhoeae* (17 strains represeenting various serotypes were tested) | 3.67–26.64 |

$^a$Samples with an S/N < 3 were defined as negative. All negative samples were tested using 10 μg of genomic DNA.
$^b$Samples with an S/N > 3 were defined as positive. All positive samples were tested using 100 ng of genomic DNA.

Due to the specificity of the SSJK1 sequence for *N. gonorrhoeae* it will be appreciated that probes based upon the entire sequence or fragments thereof may be used in other DNA hybridization assays. Accordingly, in general DNA probes based upon the SSJK1 sequence are intended to be within the invention. Such probes may be labeled directly or indirectly depending upon the particular hybridization assay format used.

10. HBV Subtype Non-specific Sandwich Hybridization Assays

Extensive comparison of the assay designed for adw HBV subtype described in part B of the results section of Example 3 above against dot blots using a $^{32}$P labeled strain adw HBV probe containing the entire genome on samples obtained in the United States revealed that the former gave a small number of false negatives. Further comparative testing of samples obtained from Japan exhibited an even greater significance of false negatives. These results indicated that it was possible that the relatively short oligonucleotide probes used in the hybridization assay were not binding to some of the samples due to strain variation at the DNA level (i.e., the samples included non-adw subtypes that varied enough to affect the binding with the oligonucleotide probes).

Accordingly, the capture and amplifier probe sets were redesigned from a computer comparison of the nucleotide sequences of the nine HBV subtypes reported in Gene Bank. These probes (subtype nonspecific, SN) are of varying length and were permitted to contain up to a 32-fold level of degeneracy (multiple nucleotides in various positions). Their 3' sequences are shown in FIG. 16. As indicated, these sequences were extended with the LLA2C and XTI 20-mers shown in FIG. 11.

Assays using these redesigned probes were compared with assays using the probes of Example 3 (adw) and dot blot. (The microtiter dish MTD format was used in the sandwich hybridizations.) The results were give below.

|      | Genomic Dot Blot | adw MTD | SN MTD |
| ---- | ---------------- | ------- | ------ |
| H 35 | +++              | ++      | +++    |
| H 36 | ++               | ++      | +++    |
| H 33 | ++               | ++      | +++    |
| H 34 | ++               | +       | +++    |
| H 32 | +++              | −       | +++    |
| H 18 | ++               | −       | ++     |
| H 21 | ++               | −       | ++     |
| H 22 | ++               | −       | +++    |
| H 23 | ++               | −       | +++    |
| H 24 | ++               | −       | ++     |
| H 25 | ++               | −       | ++     |
| H 27 | ++               | −       | ++     |
| H 28 | ++               | −       | ++     |
| H 31 | ++               | −       | +      |
| 3    | +++              | −       | ++     |
| 5    | ++               | −       | +      |
| 6    | ++               | −       | +      |
| 15   | +++              | −       | +++    |
| 17   | +++              | −       | ++     |
| 42   | ++               | −       | +++    |
| 48   | ++               | −       | +++    |
| adr  | +                | −       | +      |
| adw  | +                | +       | +      |

As mentioned, the adw assay negative samples were positive in the SN assay and genomic dot blot—indicating the samples are subtype other than adw. A sample of known adr subtype was employed as a control.

It will be appreciated that the invention assay may be adapted to conduct multiple assays for different analytes simultaneously. In one format, by changing the label and the labeling probe sequences, amplification multimer and labeled probe sequences for a new analyte, it should prove possible to detect two different analytes in the same sample on the same solid phase. Alternatively, by synthesizing analyte specific capture probe and attaching the specific complementary capture probes to different positions on a membrane strip, it is possible to perform several different assays simultaneously with the same label.

Due to the low interference observed from the presence of heterologous nucleic acids and sample components, the invention method presented here is useful in the detection of a variety of organisms in crude materials with minimal sample preparation. Except for the solution phase hybridization probes which are unmodified synthetic oligonucleotides, all assay components are universal (analyte sequence independent); therefore, a new assay simply requires a new set of oligonucleotides. In principle, the chemiluminescent form of the analysis system presented is sufficiently sensitive to permit single gene detection in 5 μg of mammalian DNA in 4 h.

Modifications of the above-described modes for carrying out the invention that are obvious to those of skill in nucleic acid chemistry, biochemical assays, and related fields are intended to be within the scope of the following claims.

We claim:

1. A synthetic branched nucleic acid multimer having a minimum of three termini comprising a combination of 5' and 3' termini comprising:
   (a) at least one first single-stranded oligonucleotide unit that is capable of hybridizing specifically to a first single-stranded nucleic acid sequence of interest; and
   (b) a multiplicity of second single-stranded oligonucleotide units that are capable of hybridizing specifically to a second single-stranded nucleic acid sequence of interest, wherein the first single-stranded oligonucleotide unit is bonded directly or indirectly to the multiplicity of second single-stranded oligonucleotide units only via covalent bonds.

2. The nucleic acid multimer of claim 1 wherein the first oligonucleotide unit has a different sequence than the second oligonucleotide unit and the number of second oligonucleotide units is at least about two-fold the number of first oligonucleotide units.

3. The nucleic acid multimer of claim 1 wherein the first oligonucleotide unit is of about 15 to 50 bases and has a GC content in the range of about 40% to about 60% and the second oligonucleotide unit is of about 15 to 50 bases and has a GC content in the range of about 40% to about 60%.

4. The nucleic acid multimer of claim 1 wherein the nucleotide sequence of the first oligonucleotide unit is the same as the nucleotide sequence of the second oligonucleotide unit and the combined number of units is at least about 3.

5. The nucleic acid multimer of claim 1 wherein the multimer has a "comb-like" branched structure and comprises an oligonucleotide backbone with one or more pendant chains composed of one or more oligonucleotide units.

6. The nucleic acid multimer of claim 1 wherein the multimer has a "fork-like" branched structure.

7. The nucleic acid multimer of claim 1 wherein the multimer is a DNA multimer.

8. The nucleic acid multimer of claim 1 wherein the multimer is an RNA multimer.

9. The nucleic acid multimer of claim 1 wherein either or both of the first and second single-stranded oligonucleotide units contains one or more modified nucleotides.

10. The nucleic acid multimer of claim 1 wherein the oligonucleotide units of the multimer are linked to each other through phosphodiester bonds.

11. The nucleic acid multimer of claim 1 wherein the oligonucleotide units of the multimer are linked to each other via a cross-linking agent.

12. The nucleic acid multimer of claim 11 wherein the cross-linking agent is covalently bonded to the oligonucleotide units of the multimer via $N^4$-modified cytosine bases.

13. The nucleic acid multimer of claim 1 wherein at least a portion of the oligonucleotide units of the multimer are linked via a multifunctional moiety derived from a compound of the formula:

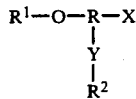 (1)

where R is an organic moiety, R¹ is a hydroxyl protecting group that can be removed under conditions that do not remove synthetic nucleic acid from a solid phase and do not remove exocyclic nitrogen or phosphate protecting groups, X is a phosphorous-containing group that facilitates nucleic acid synthesis, Y is a radical derived from a nucleophilic group, and R² is R¹ or a blocking or protective group that can be removed and replaced with hydrogen without affecting R¹.

14. The nucleic acid multimer of claim 1 wherein at least a portion of the oligonucleotide units are linked via a multifunctional moiety derived from a compound of the formula:

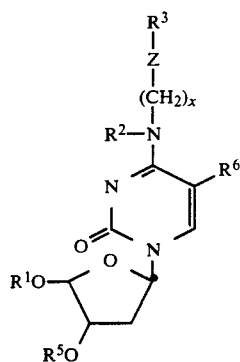 (2)

where Z is a nucleophile, R¹ is a protective group that is generally base-stable and acid sensitive, R² is hydrogen or methyl, R³ is a protective group that can be removed and replaced with hydrogen without affecting R¹, R⁵ is a phosphorus derivative that enables addition of nucleotides to the 5' position of an oligonucleotide chain during chemical synthesis, R⁶ is methyl, hydrogen, I, Br, or F, and X is an integer in the range of 1 to 8, inclusive.

15. The nucleic acid multimer of claim 1 wherein at least a portion of the oligonucleotide units are linked via a multifunctional moiety derived from a compound of the formula:

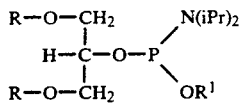

where R is a hydroxyl protecting group, iPr is isopropyl, and R¹ is methyl or beta-cyanoethyl.

16. The nucleic acid multimer of claim 1 wherein the first single-stranded nucleotide sequence of interest is analyte nucleic acid.

17. The nucleic acid multimer of claim 1 wherein the first single-stranded nucleotide sequence of interest is an oligonucleotide that is hybridized to analyte nucleic acid.

18. The nucleic acid multimer of claim 1 wherein the first single-stranded nucleotide sequence of interest is an oligonucleotide that is bound to a ligand.

19. The nucleic acid multimer of claim 1 wherein the second single-stranded nucleotide sequence of interest is a sequence of a single-stranded labeled oligonucleotide.

20. The nucleic acid multimer of claim 1 wherein the second single-stranded nucleotide sequence of interest is a sequence of an oligonucleotide unit of a second nucleic acid multimer.

21. The nucleic acid multimer of claim 1 wherein there is a chemically cleavable linker in each of the second single-stranded oligonucleotide units.

22. The nucleic acid multimer of claim 19 wherein there is a chemically cleavable linker in each of the second single stranded oligonucleotide units.

23. The nucleic acid multimer of claim 21 wherein the linker includes a 1,2-diol group that is cleavable with a periodate.

24. The nucleic acid multimer of claim 22 wherein the linker includes a 1,2-diol group that is cleavable with a periodate.

25. The nucleic acid multimer of claim 23 wherein the linker has the formula:

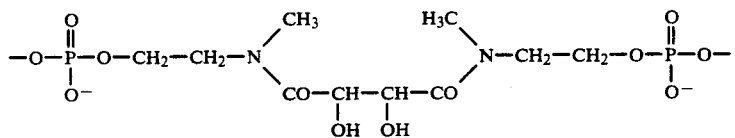

26. The nucleic acid multimer of claim 24 wherein the linker has the formula:

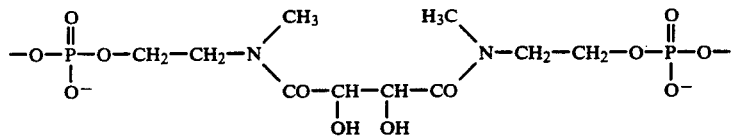

27. A nucleic acid hybridization assay wherein:
(a) the multimer of claim 19 is hybridized via the first oligonucleotide unit to single-stranded analyte nucleic acid bound to a solid phase or to a single-stranded oligonucleotide bound to the analyte, or to a second multimer bound to the analyte;
(b) unbound multimer is removed;
(c) single-stranded labeled oligonucleotide is hybridized to the multimer via the second oligonucleotide
(d) unbound labeled oligonucleotide is removed;

(e) the presence of label bound to the multimer is detected.

28. The assay of claim 27 wherein the first oligonucleotide unit has a different sequence than the second oligonucleotide unit and the number of second oligonucleotide units is at least about two-fold the number of first oligonucleotide units.

29. The assay of claim 27 wherein the first oligonucleotide unit is of about 15 to 50 bases and has a GC content in the range of about 40% to about 60% and the second oligonucleotide unit is of about 15 to 50 bases and has a GC content in the range of about 40% to about 60%.

30. The assay of claim 27 wherein the nucleotide sequence of the first oligonucleotide unit is the same as the nucleotide sequence of the second oligonucleotide unit and the combined number of units is at least about 3.

31. The assay of claim 27 wherein the oligonucleotide units of the multimer are linked to each other through phosphodiester bonds.

32. The assay of claim 27 wherein the oligonucleotide units of the multimer are linked to each other via a cross-linking agent.

33. The assay of claim 32 wherein the cross-linking agent is covalently bonded to the oligonucleotide units of the multimer via $N^4$-modified cytosine bases.

34. The assay of claim 32 wherein at least a portion of the oligonucleotide units of the multimer are linked via a multifunctional moiety derived from a compound of the formula:

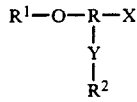

(1)

where R is an organic moiety, $R^1$ is a hydroxyl protecting group that can be removed under conditions that do not remove synthetic nucleic acid from a solid phase and do not remove exocyclic nitrogen or phosphate protecting groups, X is a phosphorous-containing group that facilitates nucleic acid synthesis, Y is a radical derived from a nucleophilic group, and $R^2$ is $R^1$ or a blocking or protective group that can be removed and replaced with hydrogen without affecting $R^1$.

35. The assay of claim 27 wherein at least a portion of the oligonucleotide units are linked via a multifunctional moiety derived from a compound of the formula:

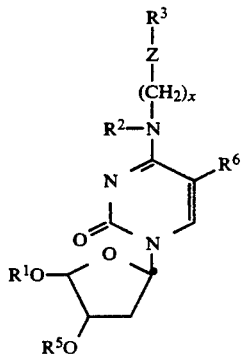

(2)

where Z is a nucleophile, $R^1$ is a protective group that is generally base-stable and acid sensitive, $R^2$ is hydrogen or methyl, $R^3$ is a protective group that can be removed and replaced with hydrogen without affecting $R^1$, $R^5$ is a phosphorus derivative that enables addition of nucleotides to the 5' position of an oligonucleotide chain during chemical synthesis, $R^6$ is methyl, hydrogen, I, Br, or F, and X is an integer in the range of 1 to 8, inclusive.

36. The assay of claim 27 wherein at least a portion of the oligonucleotide units are linked via a multifunctional moiety derived from a compound of the formula:

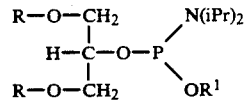

where R is a hydroxyl protecting group, iPr is isopropyl, and $R^1$ is methyl or beta-cyanoethyl.

37. A solution sandwich nucleic acid hybridization assay for detecting a first nucleic acid sequence that is part of a nucleic acid segment that includes a second nucleic acid sequence in a sample that contains said segment and another nucleic acid segment that comprises the first nucleic acid sequence but does not include the second nucleic acid sequence comprising:

(a) contacting the analyte under hybridizing conditions with an excess of (i) an amplifier probe oligonucleotide comprising a first segment that is complementary to one of the first nucleic acid sequence or the second nucleic acid sequence and a second segment that is complementary to an oligonucleotide unit of a nucleic acid multimer and (ii) a capture probe oligonucleotide comprising a first segment that is complementary to the other of the first nucleic acid sequence or the second nucleic acid sequence and a second segment that is complementary to an oligonucleotide bound to a solid phase;

(b) contacting under hybridizing conditions the product of step (a) with the oligonucleotide bound to the solid phase;

(c) thereafter separating materials not bound to the solid phase;

(d) contacting under hybridizing conditions the solid phase complex product of step (c) with the nucleic acid multimer, said multimer comprising (i) at least one oligonucleotide unit that is complementary to the second segment of the amplifier probe oligonucleotide and (ii) a multiplicity of second oligonucleotide units that are complementary to a labeled oligonucleotide;

(e) removing unbound multimer;

(f) contacting under hybridizing conditions the solid phase complex product of step (e) with the labeled oligonucleotide;

(g) removing unbound labeled oligonucleotide; and (h) detecting the presence of label in the solid phase complex product of step (g).

38. An immunoassay for an analyte molecule comprising:

(a) binding a ligand specifically and directly or indirectly to the analyte, said ligand having a single-stranded oligonucleotide that is complementary to the first oligonucleotide unit of the multimer of claim 1 bound thereto;

(b) removing unbound ligand;

(c) hybridizing the multimer of claim 1 to the ligand;

(d) hybridizing a labeled oligonucleotide to the second oligonucleotide units of the bound multimer;
(e) removing unbound labeled oligonucleotide;
(f) detecting the presence of label bound to the bound multimer.

39. A synthetic linear nonhomopolymeric nucleic acid multimer useful as a means for amplifying a detectable signal in an assay involving nucleic acid hybridization consisting essentially of:
(a) at least one first single-stranded oligonucleotide unit that is capable of hybridizing specifically to a first single-stranded nucleic acid sequence of interest; and
(b) a multiplicity of second single-stranded oligonucleotide units all of which are capable of hybridizing specifically to a second single-stranded nucleic acid sequence of interest, wherein the first single-stranded oligonucleotide unit is bonded directly or indirectly to the multiplicity of second single-stranded oligonucleotide units only via covalent bonds.

40. The nucleic acid multimer of claim 39 wherein the first oligonucleotide unit has a different sequence than the second oligonucleotide unit and the number of second oligonucleotides units is at least about two-fold the number of first oligonucleotide units.

41. The nucleic acid multimer of claim 39 wherein the first oligonucleotide unit has about 15 to 30 bases and has a GC content in the range of about 40% to about 60% and the second oligonucleotide unit is of about 15 to 30 bases and has a GC content in the range of about 40% to about 60%.

42. The nucleic acid multimer of claim 39 wherein the nucleotide unit sequence of the first oligonucleotide unit is the same as the nucleotide sequence of the second oligonucleotide unit and the combined number of units is at least about 3.

43. The nucleic acid multimer of claim 39 wherein the multimer is a DNA multimer.

44. The nucleic acid multimer of claim 39 wherein the multimer is an RNA multimer.

45. The nucleic acid multimer of claim 39 wherein either or both of the first and second single-stranded oligonucleotide units contains one or more modified nucleotides.

46. The nucleic acid multimer of claim 39 wherein the oligonucleotide units of the multimer are linked to each other through phosphodiester bonds.

47. The nucleic acid multimer of claim 39 wherein the oligonucleotide units of the multimer are linked to each other via a cross-linking agent.

48. The nucleic acid multimer of claim 39 wherein the first single-stranded nucleotide sequence of interest is analyte nucleic acid.

49. The nucleic acid multimer of claim 39 wherein the first single-stranded nucleotide sequence of interest is an oligonucleotide that is hybridized to analyte nucleic acid.

50. The nucleic acid multimer of claim 39 wherein the first single-stranded nucleotide sequence of interest is an oligonucleotide that is bound to a ligand.

51. The nucleic acid multimer of claim 39 wherein the second single-stranded nucleotide sequence of interest is a sequence of a single-stranded labeled oligonucleotide.

52. The nucleic acid multimer of claim 39 wherein the second single-stranded nucleotide sequence of interest is a sequence of an oligonucleotide unit of a second nucleic acid multimer.

53. A nucleic acid hybridization assay wherein:
(a) the multimer of claim 51 is hybridized via the first oligonucleotide unit to single-stranded analyte nucleic acid bound to a solid phase or to a single-stranded oligonucleotide bound to the analyte;
(b) unbound multimer is removed;
(c) single-stranded labeled oligonucleotide is hybridized to the multimer via the second oligonucleotide units;
(d) unbound labeled oligonucleotide is remove; and
(e) the presence of label bound to the multimer is detected.

54. The assay of claim 53 wherein the first oligonucleotide unit has a different sequence than the second oligonucleotide unit and the number of second oligonucleotide units is at least about two-fold the number of first oligonucleotide units.

55. The assay of claim 53 wherein the oligonucleotide units of the multimer are linked directly to each other through phosphodiester bonds.

56. The assay of claim 53 wherein the oligonucleotide units of the multimer are linked to each other via a cross-linking agent.

57. The assay of claim 38 wherein the analyte molecule is an antigen and the ligand is an antibody.

58. An assay for an analyte molecule comprising:
(a) binding a ligand specifically and directly or indirectly to the analyte, said ligand having a single-stranded oligonucleotide that is complementary to the first oligonucleotide unit of the multimer of claim 39 bound thereto;
(b) removing unbound ligand;
(c) hybridizing the multimer of claim 39 to the ligand;
(d) hybridizing a labeled oligonucleotide to the second oligonucleotide units of the bound multimer;
(e) removing unbound labeled oligonucleotide;
(f) detecting the present of label bound to the bound multimer.

59. The assay of claim 58 wherein the analyte molecule is an antigen and the ligand is an antibody.

* * * * *